US006989242B1

(12) United States Patent
Moore et al.

(10) Patent No.: US 6,989,242 B1
(45) Date of Patent: Jan. 24, 2006

(54) CAR RECEPTORS AND RELATED MOLECULES AND METHODS

(75) Inventors: David D. Moore, Bellaire, TX (US); Hueng-Sik Choi, Kwangju (KR); Myriam I. Baes, Blanden (BE)

(73) Assignee: The General Hospital Coporation, Boston, MA (US)

( * ) Notice: Subject to any disclaimer, the term of this patent is extended or adjusted under 35 U.S.C. 154(b) by 816 days.

(21) Appl. No.: 08/934,388

(22) Filed: Sep. 19, 1997

Related U.S. Application Data

(63) Continuation-in-part of application No. 07/843,350, filed on Feb. 26, 1992, now Pat. No. 5,756,448.

(51) Int. Cl.
*G01N 33/53* (2006.01)
*G01N 33/566* (2006.01)

(52) U.S. Cl. .......................... 435/7.8; 435/7.1; 435/7.2; 435/69.1

(58) Field of Classification Search ............... 435/69.1, 435/7.1, 7.8, 7.2
See application file for complete search history.

(56) References Cited

U.S. PATENT DOCUMENTS

| | | | | |
|---|---|---|---|---|
| 4,870,009 A | 9/1989 | Evans et al. | ................... | 435/70 |
| 4,981,784 A | 1/1991 | Evans et al. | ................... | 435/6 |
| 5,071,773 A | 12/1991 | Evans et al. | ................ | 436/501 |
| 5,077,211 A | 12/1991 | Yarosh | ........................ | 435/193 |
| 5,183,736 A | 2/1993 | Pfahl et al. | .................... | 435/6 |
| 5,756,448 A | * 5/1998 | Moore et al. | ................... | 514/2 |

FOREIGN PATENT DOCUMENTS

| | | |
|---|---|---|
| WO | WO 90/06318 | 6/1990 |
| WO | WO 90/07517 | 7/1990 |
| WO | WO 90/11273 | 10/1990 |
| WO | WO 90/14356 | 11/1990 |
| WO | WO 90/15815 | 12/1990 |
| WO | WO 91/07488 | 5/1991 |
| WO | WO 91/12258 | 8/1991 |
| WO | WO 91/14695 | 10/1991 |
| WO | WO 93/17041 | 9/1993 |
| WO | WO96/36230 | * 11/1996 |

OTHER PUBLICATIONS

Choi et al., "Differential transactivation by two isoforms of the orphan nuclear hormone receptor CAR," J. Biol. Chem. 272:23565–23571, 1997.

Bugge et al, "RXRα, a promiscuous partner of retinoic acid and thyroid hormone receptors," *The EMBO Journal* 11:1409–1418, 1992.

Danielian et al., "Identification of a conserved region required for hormone dependent transcriptional activation by steroid hormone receptors," *The EMBO Journal* 11:1025–1033, 1992.

Evans, "The Steroid and Thyroid Hormone Receptor Superfamily," *Science* 240:889–895, 1988.

Forman et al., "Interactions Among a Subfamily of Nuclear Hormone Receptors: The Regulatory Zipper Model," *Molecular Endocrinology* 4:1293–1301, 1990.

Forman et al., "A Domain Containing Leucine–Zipper–Like Motifs Mediate Novel in Vivo Interactions between the Thyroid Hormone and Retinoic Acid Receptors," *Molecular Endocrinology* 3:1610–1626, 1989.

Fuller, "The steroid receptor superfamily: mechanisms of diversity," *The FASEB Journal* 5:3092–3099, 1991.

Gebert et al., "High frequency of retinoic acid receptor β abnormalities in human lung cancer," *Oncogene* 6:1859–1868, 1991.

Kumar et al., "Functional Domains of the Human Estrogen Receptor," *Cell* 51:941–951, 1987.

Perlmann et al., "Two Distinct Dimerization Interfaces Differentially Modulate Target Gene Specificity of Nuclear Hormone Receptors," *Molecular Endocrinology* 10:958–966, 1996.

Smith et al., "A novel nuclear receptor superfamily member in *Xenopus* that associates with RXR, and shares extensive sequence similarity to the mammalian vitamin D3 receptor," *Nucleic Acids Research* 22:66–71, 1994.

Gen Bank sequence, accession No. AF009326, Dec. 25, 1997.

Gen Bank sequence, accession No. AF009328, Jul. 22, 1997.

Gen Bank sequence , accession No. AF009327, Jul. 22, 1997.

* cited by examiner

*Primary Examiner*—Michael Pak
(74) *Attorney, Agent, or Firm*—Clark & Elbing LLP

(57) ABSTRACT

Purified DNA encoding CAR receptors and the recombinant proteins expressed from such DNA are disclosed. The recombinant receptor polypeptides are used to identify CAR ligands and CAR receptor binding sites and are also used to produce therapeutics. Antibodies specific for CAR receptor polypeptides are also disclosed.

8 Claims, 12 Drawing Sheets

```
GTGAGCTTGC TCCTTAAGTT ACAGGAACTC TCCTTATAAT AGACACTTCA TTTTCCTAGT

CCATCCCTCA TGAAAAATGA CTGACCACTG CTGGGCAGCA GGAGGGATGA TAATCCTAAC

TCCAATCACT GGCAACTCCT GAGATCAGAG GAAAACCAGC AACAGCGTGG GAGTTTGGGG

AGAGGCATTC CATACCAGAT TCTGTGGCCT GCAGGTGACA TGCTGCCTAA GAGAAGCAGG

AGTCTGTGAC AGCCACCCCA ACACGTGACG TC
```

| ATG | GCC | AGT | AGG | GAA | GAT | GAG | CTG | AGG | AAC | TGT | GTG | GTA | TGT | GGG | GAC |
|---|---|---|---|---|---|---|---|---|---|---|---|---|---|---|---|
| Met | Ala | Ser | Arg | Glu | Asp | Glu | Leu | Arg | Asn | Cys | Val | Val | Cys | Gly | Asp |
| 1 | | | | 5 | | | | | 10 | | | | | 15 | |

| CAA | GCC | ACA | GGC | TAC | CAC | TTT | AAT | GCG | CTG | ACT | TGT | GAG | GGC | TGC | AAG |
|---|---|---|---|---|---|---|---|---|---|---|---|---|---|---|---|
| Gln | Ala | Thr | Gly | Tyr | His | Phe | Asn | Ala | Leu | Thr | Cys | Glu | Gly | Cys | Lys |
| | | | 20 | | | | | 25 | | | | | 30 | | |

| GGT | TTC | TTC | AGG | AGA | ACA | GTC | AGC | AAA | AGC | ATT | GGT | CCC | ACC | TGC | CCC |
|---|---|---|---|---|---|---|---|---|---|---|---|---|---|---|---|
| Gly | Phe | Phe | Arg | Arg | Thr | Val | Ser | Lys | Ser | Ile | Gly | Pro | Thr | Cys | Pro |
| | | 35 | | | | | 40 | | | | | 45 | | | |

| TTT | GCT | GGA | AGC | TGT | GAA | GTC | AGC | AAG | ACT | CAG | AGG | CGC | CAC | TGC | CCA |
|---|---|---|---|---|---|---|---|---|---|---|---|---|---|---|---|
| Phe | Ala | Gly | Ser | Cys | Glu | Val | Ser | Lys | Thr | Gln | Arg | Arg | His | Cys | Pro |
| | 50 | | | | | 55 | | | | | 60 | | | | |

| GCC | TGC | AGG | TTG | CAG | AAG | TGC | TTA | GAT | GCT | GGC | ATG | AGG | AAA | GAC | ATG |
|---|---|---|---|---|---|---|---|---|---|---|---|---|---|---|---|
| Ala | Cys | Arg | Leu | Gln | Lys | Cys | Leu | Asp | Ala | Gly | Met | Arg | Lys | Asp | Met |
| 65 | | | | 70 | | | | | 75 | | | | | 80 | |

| ATA | CTG | TCG | GCA | GAA | GCC | CTG | GCA | TTG | CGG | CGA | GCA | AAG | CAG | GCC | CAG |
|---|---|---|---|---|---|---|---|---|---|---|---|---|---|---|---|
| Ile | Leu | Ser | Ala | Glu | Ala | Leu | Ala | Leu | Arg | Arg | Ala | Lys | Gln | Ala | Gln |
| | | | | 85 | | | | | 90 | | | | | 95 | |

| CGG | CGG | GCA | CAG | CAA | ACA | CCT | GTG | CAA | CTG | AGT | AAG | GAG | CAA | GAA | GAG |
|---|---|---|---|---|---|---|---|---|---|---|---|---|---|---|---|
| Arg | Arg | Ala | Gln | Gln | Thr | Pro | Val | Gln | Leu | Ser | Lys | Glu | Gln | Glu | Glu |
| | | | 100 | | | | | 105 | | | | | 110 | | |

| CTG | ATC | CGG | ACA | CTC | CTG | GGG | GCC | CAC | ACC | CGC | CAC | ATG | GGC | ACC | ATG |
|---|---|---|---|---|---|---|---|---|---|---|---|---|---|---|---|
| Leu | Ile | Arg | Thr | Leu | Leu | Gly | Ala | His | Thr | Arg | His | Met | Gly | Thr | Met |
| | | 115 | | | | | 120 | | | | | 125 | | | |

| TTT | GAA | CAG | TTT | GTG | CAG | TTT | AGG | CCT | CCA | GCT | CAT | CTG | TTC | ATC | CAT |
|---|---|---|---|---|---|---|---|---|---|---|---|---|---|---|---|
| Phe | Glu | Gln | Phe | Val | Gln | Phe | Arg | Pro | Pro | Ala | His | Leu | Phe | Ile | His |
| | 130 | | | | | 135 | | | | | 140 | | | | |

| CAC | CAG | CCC | TTG | CCC | ACC | CTG | GCC | CCT | GTG | CTG | CCT | CTG | GTC | ACA | CAC |
|---|---|---|---|---|---|---|---|---|---|---|---|---|---|---|---|
| His | Gln | Pro | Leu | Pro | Thr | Leu | Ala | Pro | Val | Leu | Pro | Leu | Val | Thr | His |
| 145 | | | | 150 | | | | | 155 | | | | | 160 | |

| TTC | GCA | GAC | ATC | AAC | ACT | TTC | ATG | GTA | CTG | CAA | GTC | ATC | AAG | TTT | ACT |
|---|---|---|---|---|---|---|---|---|---|---|---|---|---|---|---|
| Phe | Ala | Asp | Ile | Asn | Thr | Phe | Met | Val | Leu | Gln | Val | Ile | Lys | Phe | Thr |
| | | | | 165 | | | | | 170 | | | | | 175 | |

Fig. 1A

```
AAG GAC CTG CCC GTC TTC CGT TCC CTG CCC ATT GAA GAC CAG ATC TCC
Lys Asp Leu Pro Val Phe Arg Ser Leu Pro Ile Glu Asp Gln Ile Ser
            180                 185                 190

CTT CTC AAG GGA GCA GCT GTG GAA ATC TGT CAC ATC GTA CTC AAT ACC
Leu Leu Lys Gly Ala Ala Val Glu Ile Cys His Ile Val Leu Asn Thr
        195                 200                 205

ACT TTC TGT CTC CAA ACA CAA AAC TTC CTC TGC GGG CCT CTT CGC TAC
Thr Phe Cys Leu Gln Thr Gln Asn Phe Leu Cys Gly Pro Leu Arg Tyr
    210                 215                 220

ACA ATT GAA GAT GGA GCC CGT GTG GGG TTC CAG GTA GAG TTT TTG GAG
Thr Ile Glu Asp Gly Ala Arg Val Gly Phe Gln Val Glu Phe Leu Glu
225                 230                 235                 240

TTG CTC TTT CAC TTC CAT GGA ACA CTA CGA AAA CTG CAG CTC CAA GAG
Leu Leu Phe His Phe His Gly Thr Leu Arg Lys Leu Gln Leu Gln Glu
                245                 250                 255

CCT GAG TAT GTG CTC TTG GCT GCC ATG GCC CTG TTC TCT CCT GAC CGA
Pro Glu Tyr Val Leu Leu Ala Ala Met Ala Leu Phe Ser Pro Asp Arg
            260                 265                 270

CCT GGA GTT ACC CAG AGA GAT GAG ATT GAT CAG CTG CAA GAG GAG ATG
Pro Gly Val Thr Gln Arg Asp Glu Ile Asp Gln Leu Gln Glu Glu Met
        275                 280                 285

GCA CTG ACT CTG CAA AGC TAC ATC AAG GGC CAG CAG CGA AGG CCC CGG
Ala Leu Thr Leu Gln Ser Tyr Ile Lys Gly Gln Gln Arg Arg Pro Arg
    290                 295                 300

GAT CGG TTT CTG TAT GCG AAG TTG CTA GGC CTG CTG GCT GAG CTC CGG
Asp Arg Phe Leu Tyr Ala Lys Leu Leu Gly Leu Leu Ala Glu Leu Arg
305                 310                 315                 320

AGC ATT AAT GAG GCC TAC GGG TAC CAA ATC CAG CAC ATC CAG GGC CTG
Ser Ile Asn Glu Ala Tyr Gly Tyr Gln Ile Gln His Ile Gln Gly Leu
                325                 330                 335

TCT GCC ATG ATG CCG CTG CTC CAG GAG ATC TGC AGC TGA GGCCATGCTC
Ser Ala Met Met Pro Leu Leu Gln Glu Ile Cys Ser
            340                 345

ACTTCCTTCC CCAGCTCACC TGGAACACCC TGGATACACT GGAGTGGGAA

AATGCTGGGA CCAAAGATTG GGCCGGGTTC AAAGGGAGCC CAGTGGTTGC AATGAAAGAC

TAAAGCAAAA C
```

Fig. 1B

```
      CTTGTTTTCCAGGCAGTGAGGACCGCAGTCCCTAATTCCTGGCAGTTCCTGAGATCTCAA
   1  ---------+---------+---------+---------+---------+---------+  60
      GAACAAAAGGTCCGTCACTCCTGGCGTCAGGGATTAAGGACCGTCAAGGACTCTAGAGTT
``` a

```
      GGAAAGCAGGGTCAGCGAGGAGGCCTGGGGAGAGGAGGCATCCTACACCCAATCTTGTGG
  61  ---------+---------+---------+---------+---------+---------+ 120
      CCTTTCGTCCCAGTCGCTCCTCCGGACCCCTCTCCTCCGTAGGATGTGGGTTAGAACACC
``` a

```
      CCTGCTGCCTAAGGGAAACAGGAGACCATGACAGCTATGCTAACACTAGAAACCATGGCC
 121  ---------+---------+---------+---------+---------+---------+ 180
      GGACGACGGATTCCCTTTGTCCTCTGGTACTGTCGATACGATTGTGATCTTTGGTACCGG
``` a
```
                              M  T  A  M  L  T  E  T  M  A   -

AGTGAAGAAGAATATGGGCCGAGGAACTGTGTGGTGTGTGGAGACCGGGCCACAGGCTAT
 181  ---------+---------+---------+---------+---------+---------+ 240
      TCACTTCTTCTTATACCCGGCTCCTTGACACACCACACACCTCTGGCCCGGTGTCCGATA
``` a
```
       S  E  E  E  Y  G  P  R  N  C  V  V  C  G  D  R  A  T  G  Y   -

CATTTCCACGCCCTGACTTGTGAGGGCTGCAAGGGCTTCTTCAGACGAACAGTCAGCAAA
 241  ---------+---------+---------+---------+---------+---------+ 300
      GTAAAGGTGCGGGACTGAACACTCCCGACGTTCCCGAAGAAGTCTGCTTGTCAGTCGTTT
``` a
```
       H  F  H  A  L  T  C  E  G  C  K  G  F  F  R  R  T  V  S  K   -

ACCATTGGTCCCATCTGTCCGTTTGCTGGAAGGTGTGAGGTCAGCAAGGCCCAGAGACGC
 301  ---------+---------+---------+---------+---------+---------+ 360
      TGGTAACCAGGGTAGACAGGCAAACGACCTTCCACACTCCAGTCGTTCCGGGTCTCTGCG
``` a
```
       T  I  G  P  I  C  P  F  A  G  R  C  E  V  S  K  A  Q  R  R   -

CACTGTCCAGCCTGCAGGTTGCAGAAGTGTCTAAATGTTGGCATGAGGAAAGACATGATA
 361  ---------+---------+---------+---------+---------+---------+ 420
      GTGACAGGTCGGACGTCCAACGTCTTCACAGATTTACAACCGTACTCCTTTCTGTACTAT
``` a
```
       H  C  P  A  C  R  L  Q  K  C  L  N  V  G  M  R  K  D  M  I   -

CTGTCAGCAGAAGCCCTGGCATTGCGGCGAGCCAGACAGGCACAGCGGCGGGCAGAGAAA
 421  ---------+---------+---------+---------+---------+---------+ 480
      GACAGTCGTCTTCGGGACCGTAACGCCGCTCGGTCTGTCCGTGTCGCCGCCCGTCTCTTT
``` a
```
       L  S  A  E  A  L  A  L  R  R  A  R  Q  A  Q  R  R  A  E  K   -

GCATCTTTGCAACTGAATCAGCAGCAGAAAGAACTGGTCCAGATCCTCCTGGGGGCCCAC
 481  ---------+---------+---------+---------+---------+---------+ 540
      CGTAGAAACGTTGACTTAGTCGTCGTCTTTCTTGACCAGGTCTAGGAGGACCCCCGGGTG
``` a
```
       A  S  L  Q  L  N  Q  Q  Q  K  E  L  V  Q  I  L  L  G  A  H   -
```

FIG. 2

(PAGE 1 OF 3)

```
     ACTCGCCATGTGGGCCCATTGTTTGACCAGTTTGTGCAGTTCAAGCCTCCAGCCTATCTG
541  ---------+---------+---------+---------+---------+---------+ 600
     TGAGCGGTACACCCGGGTAACAAACTGGTCAAACACGTCAAGTTCGGAGGTCGGATAGAC
``` a      T   R   H   V   G   P   L   F   D   Q   F   V   Q   F   K   P   P   A   Y   L   -

```
     TTCATGCATCACCGGCCTTTCCAGCCTCGGGGCCCCGTGTTGCCTCTGCTCACACACTTT
601  ---------+---------+---------+---------+---------+---------+ 660
     AAGTACGTAGTGGCCGGAAAGGTCGGAGCCCCGGGGCACAACGGAGACGAGTGTGTGAAA
``` a      F   M   H   H   R   P   F   Q   P   R   G   P   V   L   P   L   L   T   H   F   -

```
     GCAGATATCAACACGTTTATGGTGCAACAGATCATCAAGTTCACCAAGGATCTGCCGCTC
661  ---------+---------+---------+---------+---------+---------+ 720
     CGTCTATAGTTGTGCAAATACCACGTTGTCTAGTAGTTCAAGTGGTTCCTAGACGGCGAG
``` a      A   D   I   N   T   F   M   V   Q   Q   I   I   K   F   T   K   D   L   P   L   -

```
     TTCCGGTCCCTAACCATGGAGGACCAGATCTCCCTtctcaagggagcggctgtggaaata
721  ---------+---------+---------+---------+---------+---------+ 780
     AAGGCCAGGGATTGGTACCTCCTGGTCTAGAGGGAagagttccctcgccgacaccttttat
``` a      F   R   S   L   T   M   E   D   Q   I   S   L   L   K   G   A   A   V   E   I   -

```
     ttgcatatctcactcaacactacgttctgtcttcaaacagagaatttcttctgtgggcct
781  ---------+---------+---------+---------+---------+---------+ 840
     aacgtatagagtgagttgtgatgcaagacagaagtttgtctcttaaagaagacacccgga
``` a      L   H   I   S   L   N   T   T   F   C   L   Q   T   E   N   F   F   C   G   P   -

```
     ctttgctacaagatggaggacgcagtccatgcagggttccagtacgagttttttggagtcg
841  ---------+---------+---------+---------+---------+---------+ 900
     gaaacgatgttctacctcctgcgtcaggtacgtcccaaggtcatgctcaaaaaacctcagc
``` a      L   C   Y   K   M   E   D   A   V   H   A   G   F   Q   Y   E   F   L   E   S   -

```
     atcctccacttccataaaaacctgaaaggactgcatctccaggagcctgagtatgtgctc
901  ---------+---------+---------+---------+---------+---------+ 960
     taggaggtgaaggtattttggactttcctgacgtagaggtcctcggactcatacacgag
``` a      I   L   H   F   H   K   N   L   K   G   L   H   L   Q   E   P   E   Y   V   L   -

```
     ATGGCTGCCACGGCCCTCTTCTCCCCTGACAGACCCGGAGTTACCCAAAGAGAAGAGATA
961  ---------+---------+---------+---------+---------+---------+ 1020
     TACCGACGGTGCCGGGAGAAGAGGGGACTGTCTGGGCCTCAATGGGTTTCTCTTCTCTAT
``` a      M   A   A   T   A   L   F   S   P   D   R   P   G   V   T   Q   R   E   E   I   -

```
      GATCAGCTACAAGAGGAGATGGCGCTGATTCTGAACAACCACATTATGGAACAACAGTCT
1021  ---------+---------+---------+---------+---------+---------+ 1080
      CTAGTCGATGTTCTCCTCTACCGCGACTAAGACTTGTTGGTGTAATACCTTGTTGTCAGA
``` a      D   Q   L   Q   E   E   M   A   L   I   L   N   N   H   I   M   E   Q   Q   S   -

FIG. 2

(PAGE 2 OF 3)

```
           CGGCTCCAAAGTCGGTTTCTGTATGCAAAGCTGATGGGCCTGCTGGCTGACCTCCGGAGT
     1081  ------------+---------+---------+---------+---------+---------+ 1140
           GCCGAGGTTTCAGCCAAAGACATACGTTTCGACTACCCGGACGACCGACTGGAGGCCTCA a          R  L  Q  S  R  F  L  Y  A  K  L  M  G  L  L  A  D  L  R  S  -

ATaaacaatgcatactcctatgaacttcagcgcttggaggaactgtctgctatgacgccg
     1141  ---------+---------+---------+---------+---------+---------+ 1200
           TAtttgttacgtatgaggatacttgaagtcgcgaacctccttgacagacgatactgcggc a          I  N  N  A  Y  S  Y  E  L  Q  R  L  E  E  L  S  A  M  T  P  - ctgctcggggagatttgcagttgaggcccaggcttgcatcctttccccagaccccaggg
     1201  ---------+---------+---------+---------+---------+---------+ 1260
           gacgagcccctctaaacgtcaactccgggtccgaacgtaggaaaggggtctgggggtccc a          L  L  G  E  I  C  S  * atacactggcctggaaagggtacagcgctggaccccacacgggaaccagcaggaaggagc
     1261  ---------+---------+---------+---------+---------+---------+ 1320
           tatgtgaccggacctttcccatgtcgcgacctggggtgtgcccttggtcgtccttcctcg a ttgggagtggcaatgaaatgctgaacagtcaaaaaaaaaaa
     1321  ---------+---------+---------+---------+- 1361
           aaccctcaccgttactttacgacttgtcagttttttttttt a
```

FIG. 2

(PAGE 3 OF 3)

FIG. 3A

```
                  1
mCAR1       1   MTAMLTLETMASEEYGPRN CVVCGDRATGYHFHALTCEGCKGFFRRTVSKTIGPICPFA    60
hCAR        ..........          R D.EL              Q  N              S    T

2
                GRCEVSKAQRRHCPACRLQKCLNVGM RKDMILSAEALALRRARQAQRRAEKASLQLNQQQ   120
mCAR1      61   S         T                      DA             K      QQTPV    SKE
hCAR
                                             3
                                             4
           121  KELVQILLGAHTRHVGPMFDQFVQFKPPAYLFMHHRPFQPRGPVLPLLTHFADINTFMVQ      180
                  E IRT             M T E    R  H I  Q LPTLA   V            L 5
           181  QIKFTKDLPLFRSLTMEDQISLLKGAAVEILHISLNTTFCLQTENFFCGPLCYKMEDAV       240
                  V       PI                 C V              Q  L    R TI   GA 6                            7
                                              GFCMQS
mCAR2      241  HAGFQYEFLESILHFHKNLKGLHLQEPEYVLMAATALFSPDRPGVTQREEIDQLQEEMAL       300
                RV  V   LLF   GT RK Q         L  M           D 8
           301  ILNNHIMEQQSRLQSRFLYAKLMGLLADLRSINNAYSYELQRLEELSAMTPLLGEICS         358
                T QSY KG  R PRD         L    E   E G QI HIQG    M    Q
```

```
-127  GAGTCTAGTAAGCAGCAGCTTTTAATGAGTCATGAGGTCCTGGCCCCTCC
-77   CCATCTGCCACCAACCAACACTTCTCGGGCATGCTAGGAACCCCCACCCC
-27   ACCCCACACCCACACCCAGGTCTTTGCCCTGGGTCCAGAGTCTGGGTCCT    23
```

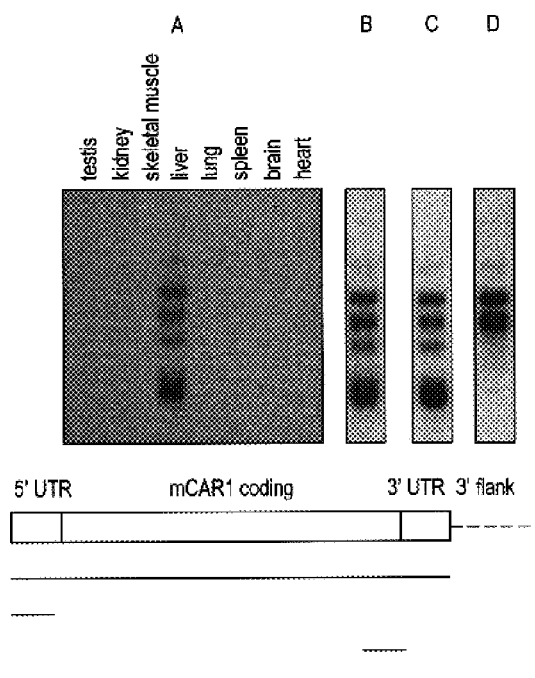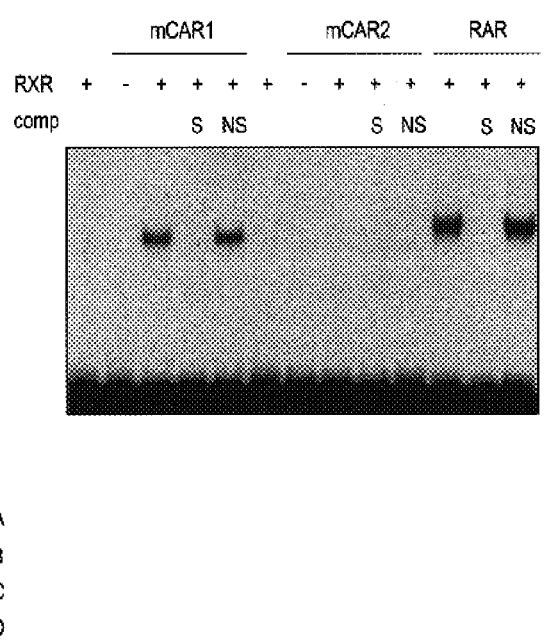
FIG. 6
FIG. 7

FIG. 9A
```
FLYAKLMGLLADIRSINNAYSYELQRLEELSAMTBLGEICS     wt mCAR1
----------------------------------A-------    L352A
-------------------------------------A---     E355A
----------------------------------------      Δ8
-------------------                           Δ27
```
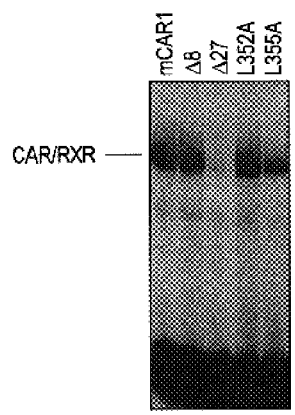
FIG. 9B
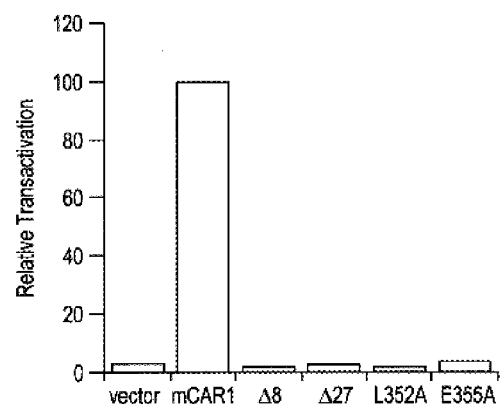
FIG. 9C

CAR RECEPTORS AND RELATED MOLECULES AND METHODS

This application is a continuation-in-part of U.S. Ser. No. 07/843,350, filed Feb. 26, 1992 now U.S. Pat. No. 5,756,448. This invention relates to receptors, particularly nuclear hormone receptors.

BACKGROUND OF THE INVENTION

In higher organisms, the nuclear hormone receptor superfamily includes approximately a dozen distinct genes that encode zinc finger transcription factors, each of which is specifically activated by binding a ligand such as a steroid, thyroid hormone (T3) or retinoic acid (RA). However, there is an additional, somewhat larger group of cDNAs that encode proteins that do not bind or respond to any known ligand. These members of the superfamily are called orphan receptors. While the role of the better characterized conventional receptors in regulating important processes in developing and adult individuals is becoming clearer, the function of the orphan receptors has been uncertain.

A number of the conventional and orphan members of the superfamily share identical or very similar amino acid sequences in an important region of the first zinc finger. Both genetic analyses and X-ray crystallography indicate that this region, termed the P box, makes sequence specific contacts with the DNA. The conventional receptors in this P box-defined subgroup include those that bind estrogen, vitamin D, T3 and RA, and nearly all of the orphan receptors identified to date also fall into this class. As a consequence of this overlap in binding specificity, many hormone response elements can bind more than one type of receptor. The best characterized of these is the element upstream of the rat growth hormone gene, which can be activated by three different isoforms of the T3 receptor encoded by two different genes and by an unknown number of retinoic acid receptor isoforms encoded by three different genes. While it does not appear to respond to the estrogen receptor or the vitamin D receptor, its response to other members of the subgroup remains uncertain.

Recently the potential complexity of the interactions of the conventional receptors with their response elements has been substantially increased by the demonstration that the three closely related RXR proteins can form heterodimers with the thyroid hormone, retinoic acid and vitamin D receptors. These heterodimers show higher binding affinity for appropriate response elements, and the RXRs are hypothesized to play central roles in signal transduction by all three classes of receptors. The impact on such heterodimers of the binding of the retinoid metabolite 9-cis retinoic acid by the RXRs remains unclear.

SUMMARY OF THE INVENTION

In general, the invention features substantially pure CAR receptor polypeptide. Preferably, such a receptor polypeptide includes an amino acid sequence substantially identical to the amino acid sequence shown in FIG. 1 (SEQ ID NO:10) or FIG. 2 (SEQ ID NO:12).

The invention further features a substantially pure polypeptide which includes a CAR receptor DNA binding domain and a CAR receptor gene activation domain (preferably, also including the ligand binding domain). Preferably, the DNA binding domain includes a sequence substantially identical to amino acids 11–75 of FIG. 1 (SEQ ID NO:10) or amino acids 21–86 of FIG. 2 (SEQ ID NO:12), or a DNA binding fragment thereof; and the gene activation or ligand binding/gene activation domain includes a sequence substantially identical to amino acids 76–348 of FIG. 1 (SEQ ID NO:10) or amino acids 182–358 or 352–357 of FIG. 2 (SEQ ID NO:12), or a gene activating fragment thereof.

In a related aspect, the invention features a substantially pure polypeptide which includes a CAR receptor heterodimerization domain.

In preferred embodiments of various aspects, the receptor polypeptide is mammalian, and preferably, human or murine.

In yet other aspects, the invention features substantially pure DNA which encodes a CAR receptor polypeptide of the invention. Preferably, such DNA is cDNA; and encodes a human or murine CAR receptor polypeptide. The invention also features a vector which includes such substantially pure DNA and which is capable of directing expression of the protein encoded by the DNA in a vector-containing cell. Finally, the invention features a cell which contains the substantially pure DNA. Preferably, the cell is a eukaryotic cell, for example, a mammalian cell.

In another aspect, the invention features a method of producing a recombinant CAR receptor polypeptide (or a fragment or analog thereof). The method involves (a) providing a cell transformed with DNA encoding a CAR receptor or a fragment or analog thereof positioned for expression is the cell; (b) culturing the transformed cell under conditions for expressing the DNA; and (c) isolating the recombinant CAR receptor polypeptide.

In yet another aspect, the invention features a substantially pure antibody which specifically binds a CAR receptor polypeptide of the invention.

In yet other aspects, the invention features therapeutic compositions which include as an active ingredient a CAR receptor polypeptide of the invention formulated in a physiologically-acceptable carrier. Such therapeutic compositions may be used in methods of treating Graves' disease or cancer (for example, lung cancer) in a mammal; such methods involve administering the therapeutic composition to the mammal in a dosage effective to decrease thyroid hormone receptor function (for the treatment of Graves' disease) or in a dosage effective to increase retinoic acid receptor expression (for the treatment of cancer).

In yet other aspects, the invention features methods of identifying a CAR ligand. One method involves (a) providing a nucleic acid sequence which encodes a CAR receptor polypeptide; (b) introducing into a host cell which is functionally deficient for CAR receptor (i) the nucleic acid which encodes the CAR receptor polypeptide (preferably, a CAR receptor polypeptide including an amino acid sequence substantially identical to the amino acid sequence shown in FIG. 1; SEQ ID NO: 10 or FIG. 2; SEQ ID NO:12) and (ii) a reporter gene operably linked to a CAR receptor polypeptide binding site (preferably, the binding site GGG-TAGGGTTCACCGAAAGTTCACTCG; SEQ ID NO: 5); (c) measuring induction of the reporter gene in the transfected host cell; (d) contacting the transfected host cell with a candidate ligand; and (e) measuring induction of said reporter gene in the presence of the candidate ligand, an increase or decrease in the induction as compared to the induction in (c) being indicative of the presence of a CAR ligand.

The second method involves (a) providing a nucleic acid sequence which encodes a CAR receptor polypeptide (preferably, including an amino acid sequence substantially identical to the amino acid sequence shown in FIG. 1; SEQ ID NO: 10 or FIG. 2; SEQ ID NO:12); (b) introducing the nucleic acid into a host cell so that the recombinant CAR receptor polypeptide is expressed; (c) isolating the recombinant protein; (d) immobilizing the recombinant protein on a solid substrate (preferably, a column); (e) contacting the immobilized recombinant protein with a candidate ligand under conditions which allow formation of an affinity complex between the immobilized recombinant CAR receptor polypeptide and the candidate ligand; and (f) detecting complex formation as an indication of the presence of a CAR ligand.

In yet other aspects, the invention features methods of identifying a CAR receptor DNA binding site. One method involves (a) providing a nucleic acid sequence which encodes a CAR receptor polypeptide (preferably including an amino acid sequence substantially identical to the amino acid sequence shown in FIG. 1; SEQ ID NO: 10 or FIG. 2; SEQ ID NO:12); (b) introducing into a host cell which is functionally deficient for CAR receptor (i) the nucleic acid which encodes the CAR receptor polypeptide and (ii) a reporter gene which is operably linked to a candidate CAR receptor DNA binding site; and (c) measuring induction of the reporter gene in the transfected host cell, induction being indicative of the presence of an operably linked CAR receptor DNA binding site.

A second method involves (a) providing a nucleic acid sequence which encodes a CAR receptor polypeptide (preferably, including an amino acid sequence substantially identical to the amino acid sequence shown in FIG. 1; SEQ ID NO: 10 or FIG. 2; SEQ ID NO:12); (b) introducing the nucleic acid into a host cell so that the recombinant CAR receptor polypeptide is expressed; (c) isolating the recombinant protein; (d) contacting the recombinant protein with a candidate DNA binding site under conditions which allow formation of an affinity complex between the recombinant CAR receptor polypeptide and the candidate binding site; and (e) detecting complex formation as an indication of the presence of a CAR receptor DNA binding site.

In a final aspect, the invention features chimeric receptors. Such chimeric receptors may include the DNA binding domain of a CAR receptor polypeptide (preferably, including a sequence substantially identical to amino acids 11–75 of FIG. 1; SEQ ID NO:10 or amino acids 21–86 of FIG. 2 SEQ ID NO:12, or a DNA binding fragment thereof) fused to the gene activation (and, preferably, the ligand binding domain) of a heterologous protein, preferably, a nuclear hormone receptor, or a protein chosen from the group consisting of: glucocorticoid receptor, α-retinoic acid receptor, β-retinoic acid receptor, γ-retinoic acid receptor, estrogen receptor, progesterone receptor, vitamin D receptor, mineralocorticoid receptor, thyroid receptor, VP 16, and GAL4; or the chimeric receptor may include the gene activation domain of a CAR receptor polypeptide (preferably, including a sequence substantially identical to amino acids 76–348 of FIG. 1; SEQ ID NO:10 or amino acids 182–358 of FIG. 2; SEQ ID NO:12, or a gene activating fragment thereof) fused to the DNA binding domain of a heterologous protein, preferably, a nuclear hormone receptor or a protein chosen from the group consisting of: glucocorticoid receptor, α-retinoic acid receptor, β-retinoic acid receptor, γ-retinoic acid receptor, estrogen receptor, progesterone receptor, vitamin D receptor, mineralocorticoid receptor, thyroid receptor, and GAL4.

By "CAR receptor polypeptide" is meant a polypeptide which is capable of binding to a DNA sequence of GGG-TAGGGTTCACCGAAAGTTCACTCG (SEQ ID NO: 5) and activating the expression of downstream genes, even when mammalian cells harboring the receptor are grown in medium containing charcoal-stripped serum; in particular, a CAR receptor polypeptide activates such gene expression in the absence of retinoic acid.

By "substantially pure" is meant that the CAR receptor polypeptide provided by the invention is at least 60%, by weight, free from the proteins and naturally-occurring organic molecules with which it is naturally associated. Preferably, the preparation is at least 75%, more preferably at least 90%, and most preferably at least 99%, by weight, CAR receptor polypeptide. A substantially pure CAR receptor polypeptide may be obtained, for example, by extraction from a natural source (e.g., a mammalian liver cell); by expression of a recombinant nucleic acid encoding a CAR receptor polypeptide, or by chemically synthesizing the protein. Purity can be measured by any appropriate method, e.g., column chromatography, polyacrylamide gel electrophoresis, or HPLC analysis. By a "polypeptide" is meant any chain of amino acids, regardless of length or post-translational modification (e.g., glycosylation).

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein or domain (assayed, e.g., as described herein). Preferably, the amino acid sequence is at least 60%, preferably, 70%, more preferably, 85%, and, most preferably, 95% identical to the sequence of either SEQ ID NO: 10 or SEQ ID NO: 12. A "substantially identical" nucleic acid sequence codes for a substantially identical amino acid sequence as defined above.

By a "DNA binding domain" is meant a stretch of amino acids which is capable of directing specific polypeptide (e.g., receptor) binding to a particular DNA sequence.

By "gene activation domain" is meant a stretch of amino acids which is capable of inducing the expression of a gene to whose control region it is bound.

By "heterodimerization domain" is meant a stretch of amino acids which is capable of directing specific complex formation with a heterologous protein; such a domain may direct the formation of dimers, trimers, tetramers, or other higher order hetero-oligomers.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a CAR receptor polypeptide.

By "positioned for expression" is meant that the DNA molecule is positioned adjacent to a DNA sequence which directs transcription and translation of the sequence (i.e., facilitates the production of, e.g., CAR receptor polypeptide).

By "a host cell which is functionally deficient for CAR receptor" is meant a cell, e.g., a mammalian cell, which exhibits little or no CAR receptor-mediated gene stimulatory activity; such activity may be measured in standard transactivation assays using, e.g., a transfected reporter gene operably linked to a CAR binding site as described herein.

By "substantially pure antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., CAR receptor-specific antibody. A substantially pure CAR receptor antibody may be obtained, for example, by affinity chromatography using recombinantly-produced CAR receptor polypeptide and standard techniques.

By "specifically binds", as used herein, is meant an antibody which recognizes and binds CAR receptor polypeptide but which does not substantially recognize and bind other molecules in a sample, e.g., a biological sample, which naturally includes CAR receptor polypeptide.

By "reporter gene" is meant a gene whose expression may be assayed; such genes include, without limitation, chloramphenicol transacetylase (CAT) and β-galactosidase.

By "operably linked" is meant that a gene and a regulatory sequence(s) are connected in such a way as to permit gene expression when the appropriate molecules (e.g., transcriptional activator proteins) are bound to the regulatory sequence(s).

By "heterologous" is meant any protein other than the human CAR receptor which includes a suitable (i.e., a DNA binding, gene activation, and/or ligand binding) domain.

Other features and advantages of the invention will be apparent from the following description of the preferred embodiments thereof, and from the claims.

DETAILED DESCRIPTION

The drawings will first briefly be described.
Drawings

FIG. 1 is the nucleic acid sequence (SEQ ID NO:1) and deduced amino acid sequence (SEQ ID NO:10) of the human CAR receptor.

FIG. 2 is the nucleic acid (SEQ ID NO:11) and deduced amino acid sequence (SEQ ID NO:12) of the murine CAR receptor mCAR1.

FIG. 3A is a schematic representation of the sequences of mCAR1 and mCAR/MB67. The sequence of mCAR1 (Genbank accession number AF009327) is shown, and differences between mCAR1 and the previously described MB67 (referred to here as hCAR) and also the mCAR2 variant (Genbank accession number AF900328) are indicated. The DNA binding domain is in bold. Dots indicate residues not present in hCAR. The positions of the introns in the mCAR gene are indicated. The first intron is 5 nucleotides upstream of the ATG encoding the first methionine. Introns that fall within a codon are indicated after the corresponding amino acid.

Figure 3B:
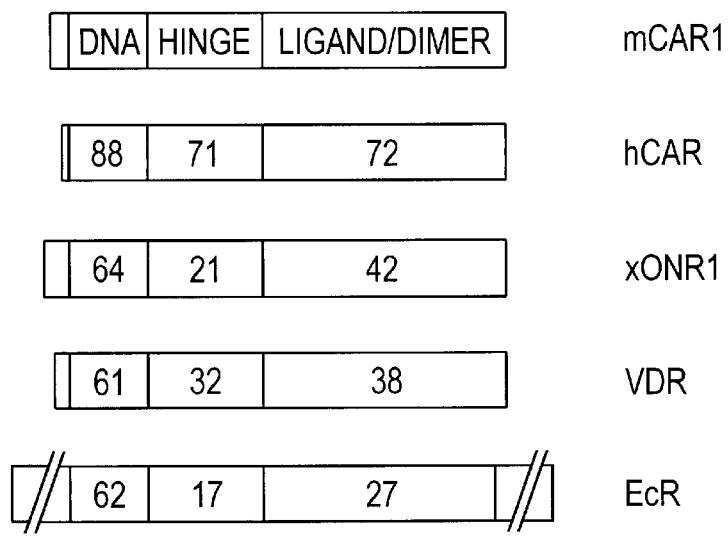

FIG. 3B is a schematic representation indicating comparisons of mCAR1 to related members of the nuclear hormone receptor superfamily. The DNA binding, hinge, and ligand binding/dimerization domains of mCAR1 are indicated, and the percent identity of the analogous domains of related proteins is indicated. VDR is the human vitamin D receptor, xONR is a *Xenopus laevis* orphan receptor (Smith et al., *Nucl. Acids Res.* 22:66–71, 1994), and EcR is the *Drosophila melanogaster* ecdysone receptor.

Figure 4A:
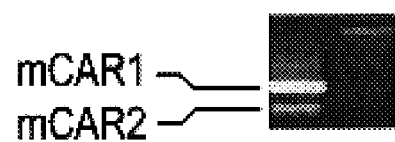
Figure 4B:
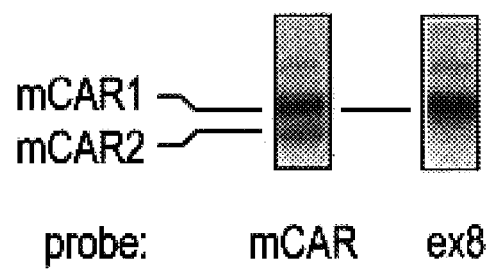

FIGS. 4A and 4B are photographs demonstrating expression of mCAR1 and mCAR2 in liver mRNA. mRNA based PCR was used to amplify mCAR sequences using primers flanking the mCAR2 deletion, with mouse liver mRNA as a template. In FIG. 4A, the positions of amplified bands of the sizes expected for mCAR1 and mCAR2 are indicated. The products of the mRNA based PCR reaction are in the left lane. Size markers are in the right lane. In FIG. 4B, an experiment is shown in which the gel in FIG. 4A was blotted and hybridized with probes corresponding to the intact mCAR ligand binding domain or just exon 8, as indicated. Control lanes showed no bands by ethidium staining or hybridization.

Figure 5A:
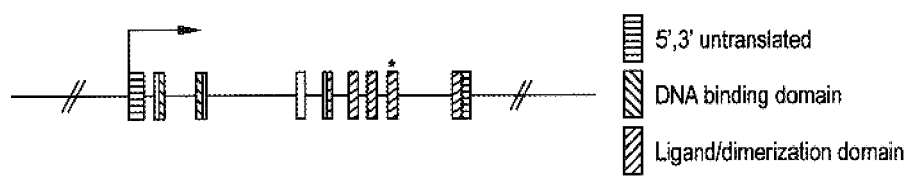

FIG. 5A is a diagram indicating the positions of the mCAR introns, 5' untranslated and 3' untranslated regions of the primary transcript, and the positions of various portions of the transcript and protein. For the 3' extended transcripts, the 3' untranslated region extends into the 3' flanking region. The 8th exon deleted in mCAR2 is indicated by a star.

Figure 5B:
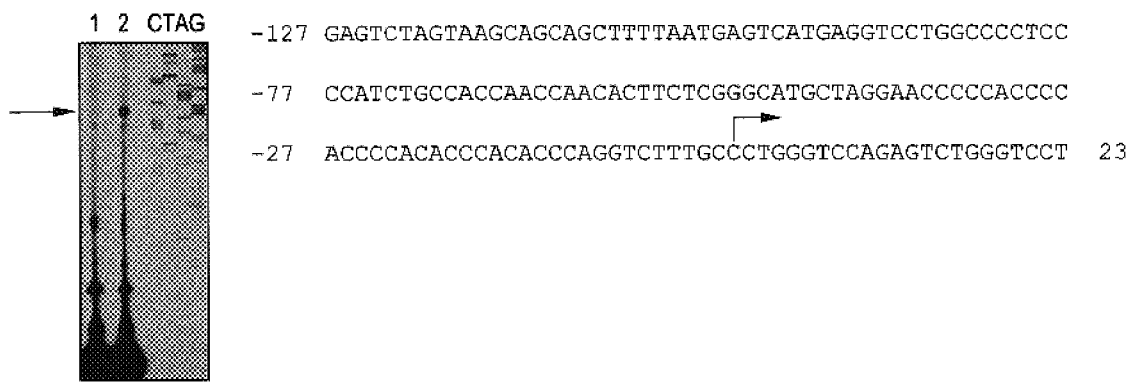

FIG. 5B is a photograph showing a primer extension analysis of mCAR transcripts. Either control RNA (lane 1) or total mouse liver RNA (lane 2) was used as a template for primer extension using a 5' end labeled mCAR primer from the 5' untranslated region. Products were resolved next to a sequence ladder generated using the same primer. The arrow indicates specifically extended product. To the right of the photograph is indicated the position of the primary transcriptional start site relative to the mCAR genomic sequence (Genbank accession number AF009326).

FIG. 6 is a photograph and diagram indicating the expression of mCAR transcripts. A Northern blot containing mouse polyA+ mRNA from various tissues (Clontech) was sequentially hybridized with either a full length mCAR probe ("A") or a series of shorter probes as indicated. Probes "B" and "C" were generated by PCR using the mCAR cDNA as a template, and probe "D" was generated by PCR using the genomic clone as a template. Only the results with liver mRNA are shown for the smaller probes. In much longer exposures of hybridizations with either the full length probe or the two probes from the 3' end, an additional transcript of approximately 2.8 kb was observed in heart, brain, skeletal muscle, and kidney.

FIG. 7 is a photograph showing DNA binding by mCAR1 and mCAR2. mCAR1, mCAR2, RXR, and RAR proteins were expressed by in vitro translation and used for electrophoretic mobility shift assays with a βRARE probe as indicated. "S" indicates competition with the βRARE oligonucleotide, and "NS" competition with a nonspecific oligonucleotide. Equivalent amounts of mCAR1, mCAR2, and RAR were used in the binding reactions, as determined by $^{35}$S-methionine labeling.

Figure 8B:
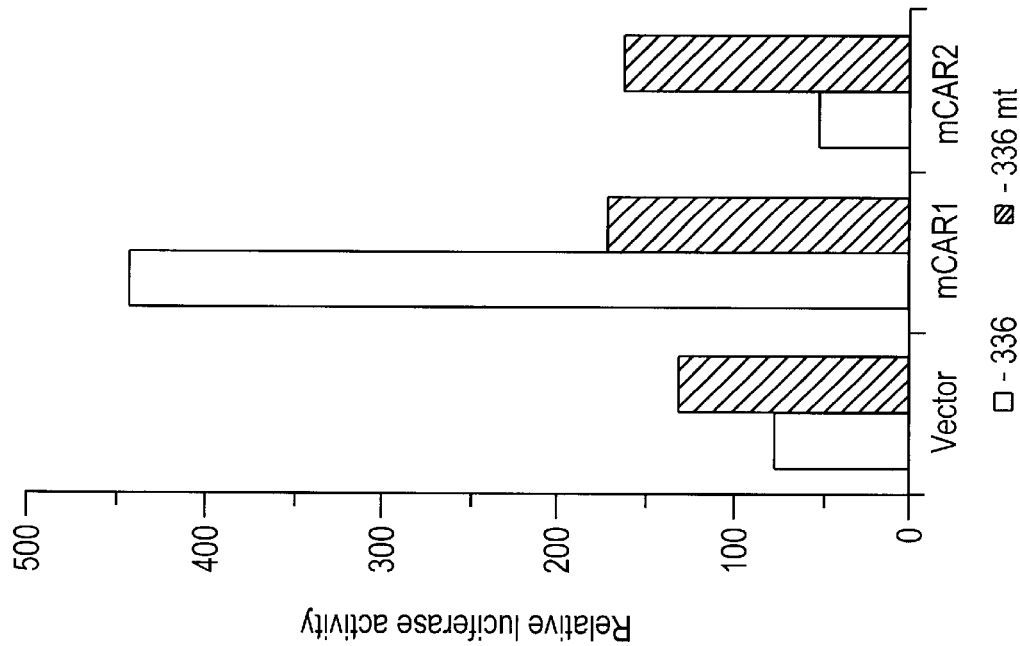
Figure 8A:
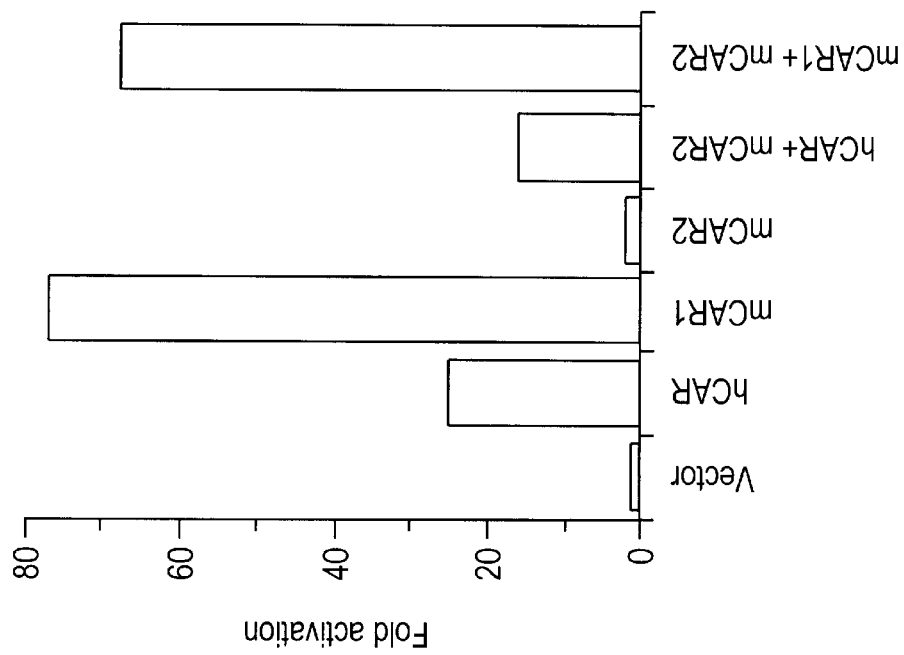

FIGS. 8A and 8B are graphs indicating transactivation by mCAR1 and mCAR2. In FIG. 8A, a luciferase reporter containing three copies of the βRARE upstream of the TK promoter was cotransfected into HepG2 cells with the indicated receptor expression vectors and a TKGH control plasmid. Normalized luciferase activity is expressed by comparison to the activity observed with the CDM8 vector alone. In FIG. 8B, two reporter constructs containing 336 bp of the RARβ2 promoter driving expression of luciferase (Moghal et al., *Mol. Cell. Biol.* 15:3945–3959 1995) were cotransfected into HepG2 cells with control, mCAR1, or mCAR2 expression vectors, as indicated, along with the TKGH internal control. In the −336 mut reporter, the βRARE was inactivated by a cluster of point mutants (Moghal et al., *Mol. Cell. Biol.* 15:3945–3959 1995). Normalized luciferase expression is presented.

FIG. 9A is a diagram showing the sequence of the AF-2 region of mCAR 1. The sequence that matches the AF-2 consensus of a glutamate flanked by paired hydrophobic residues (Danielian et al., *EMBO J.* 11:1025–1033, 1992) is in bold, and a sequence that corresponds to the 9th heptad in TR and other receptors (Forman et al., *Mol. Endocrinol.* 4:1293–1302, 1990) is underlined. Mutations introduced into the mCAR1 sequence are indicated; dashes represent residues present in the mutant proteins.

FIG. 9B is a photograph showing transactivation by mCAR1 and AF-2 mutants. HepG2 cells were cotransfected with either the CDM8 vector alone or the vectors expressing the indicated CAR proteins, the βRARE-TKluc reporter, and a TKGH internal control. Expression relative to the wild type mCAR1 is indicated.

FIG. 9C is a graph indicating DNA binding by mCAR mutants. Whole cell extracts from COSM6 cells transfected with expression vectors for the indicated mCAR proteins were incubated with analogous extracts from RXR transfected cells and the βRARE oligonucleotide, and specific complexes were resolved by electrophoretic mobility shift.

There now follows a description of the cloning and characterization of human and murine CAR receptor-encoding cDNAs useful in the invention. This example is provided for the purpose of illustrating the invention, and should not be construed as limiting.

Isolation of the Human CAR Receptor

A human liver cDNA library was screened by standard techniques with the following degenerate oligonucleotide probe: TG C/T GAG GGI TG C/T AAG G G/C ITT C/T TT C/T A/C G (SEQ ID NO. 2). This probe was based on the sequence of the P box of the thyroid/retinoid receptor subgroup, the most highly conserved portion of the DNA binding domain. As expected, a number of clones encoding previously described members of the nuclear receptor superfamily were isolated. Based on limited sequence analysis (by standard techniques), one clone that did not correspond to any previously reported cDNA was chosen for further analysis. The complete sequence of this cDNA is presented in FIG. 1 (SEQ ID NO:1).

As indicated in FIG. 1, this cDNA encodes a protein of 348 amino acids that contains conserved features of the nuclear receptor superfamily in both the DNA binding (C) domain and the putative ligand binding/dimerization (E) domain. Because of the activities of this protein described below, it is called CAR (Constitutive Activator of Retinoic acid response elements). CAR is one of the smallest superfamily members, with the shortest known A/B domain.

As expected from the oligonucleotide used for screening, the sequence of the P box DNA binding specificity determining region of the first zinc finger placed CAR in the thyroid/retinoid group. CAR was not strongly related to any other superfamily member, but was most similar to the vitamin D receptor, sharing 42 identical amino acids out of 66 in the C domain (64%), and 61/152 in the E domain (40%). This is quite similar to the relationship between the thyroid hormone and retinoic acid receptors: TRβ and RARβ which share 60% and 40% sequence identity in the C and E domains, respectively. By comparison, the closely related human TRα and TRβ receptors share 90% and 85% identity in the C and E domain. CAR also shows significant similarity to the *Drosophila melanogaster* ecdysone receptor (62% in the C domain, 29% in the E domain), making it the third member of a divergent subgroup in the superfamily. Southern blot analysis (by standard techniques) indicated that CAR may not be a member of a closely related subgroup like the TRs and the RARs.

Like a number of other members of the superfamily, CAR has a relatively long 5' untranslated region that contains several AUGs upstream of the start of the open reading frame. The function of this region is unknown.

Northern blot analysis (using standard techniques) indicated that CAR mRNA is expressed in a variety of human tissues, but is most abundant in liver. Multiple RNA species were observed, but the nature of these different species is not clear. Based on the multiple products expressed by genes encoding other superfamily members, it may well reflect alternative splicing or promoter utilization. CAR mRNA is also observed in a number of human cell lines, including HepG2 (hepatoma), JEG-3 (choriocarcinoma), and HeLa.

Ligand-Independent Transcriptional Activation by the Human CAR Ligand/Dimerization Domain To study the function of the putative ligand binding domain of the orphan, a chimeric receptor consisting of the C-terminal D, E and F domains of CAR (i.e., approximately amino acids 76–172, 173–319, and 320–348 of the CAR sequence, respectively) fused to the N-terminal A/B and C domains of TRβ was generated (termed TR/CAR), along with a control hybrid with the A/B and C domains of TR and the D, E and F domain of the glucocorticoid receptor (TR/GR). Vectors expressing these chimeras or the intact TR were cotransfected into JEG3 cells (ATCC Accession No: HTB 36) with reporter plasmids containing T3REs (i.e., of sequence AAAGGTAAGATCAGGGACGTGACCGCAG; SEQ ID NO: 3) or GREs (from the MMTV promoter as described in Chandler et al., *Cell* 33:489, 1989) upstream of a reporter gene whose expression could be assayed. Transfections were carried out in the presence of serum treated with activated charcoal to remove T3 as well as other low molecular weight hydrophobic compounds that could act as CAR ligands.

Results from such an analysis revealed that both TR and the TR/GR chimera behaved as ligand-dependent transactivators, as expected. The relatively low but reproducible level of activation conferred by TR/GR is consistent with a previous report, and is thought to be a consequence of the absence from this hybrid of transcriptional activation domains present in the A/B domain of the intact GR and the F domain of the intact TR.

In contrast, the TR/CAR chimera activated expression of the T3RE containing reporter in the absence of any added ligand. This effect was not altered by addition of T3, astraddle, testosterone, resinoid acid, or dexamethasone, or by the addition of the orphan receptor ligand 25-hydroxy cholesterol. The constitutive activation conferred by this hybrid was substantial, corresponding to greater than 50% of the response of the intact TRY. Similar results were observed with an analogous GO/CAR chimera in cotransfections with an MMTV/CAT reporter.

The activation conferred by the TR/CAR chimera in the presence of charcoal-stripped serum could be a consequence of either a direct, constitutive transcriptional activation function in the D, E or F domains of the orphan, or the presence of an uncharacterized ligand in the medium of the growing cells. To minimize the possibility of the presence of such a ligand in the media, the transfections were repeated in the absence of serum. Such conditions substantially reduced the level of both control and T3-activated expression, but did not prevent the constitutive activation function conferred by the TR/CAR chimera. Because of the substantial changes in the levels of expression from control promoters, the significance of the apparent decrease in constitutive activity relative to the level of activation conferred by TRY in the presence of hormone is uncertain. This apparent decrease may reflect the absence of some specific stimulator of CAR function present in serum or could be a less specific effect associated with the unfavorable growth conditions.

Activation of Resinoid Acid Response Elements by Human CAR

Based on the constitutive activity of the TR/CAR chimera and the similarity of the DNA binding domain of CAR to other members of the superfamily, a number of response elements were screened for activation by the intact orphan in standard cotransfections. Despite the relatively close sequence relationship between CAR and the vitamin D receptor, no response was seen with the combined vitamin D/RA response element from the rat osteocalcin gene (i.e., of sequence TGGGTGAATGAGGACATTACTGAC-CGCTCCG; SEQ ID NO: 4). However, CAR did transactivate two wild type elements, the RAREs from the RARβ gene and the alcohol dehydrogenase (ADH) gene (i.e., GGGTAGGGTTCACCGAAAGTTCACTCG; SEQ ID NO: 5). RAREs which were not transactivated by CAR included a potent up mutant version of the rat growth hormone gene T3RE/RARE (i.e., of sequence AAAGGTAAGATCAGG-GACGTGACCTCAG; SEQ ID NO:6; in tandem copies with the second copy inverted; described in Brent et al., *Mol. Endocrinol.* 3:1996, 1989) and the wild type version of the laminin T3RE/RARE (i.e., of sequence AGACAGGT-TGACCCTTTTTCTAAGGGCTTAAC-CTAGCTCACCTG; SEQ ID NO: 8). The rat malic enzyme T3RE (i.e., of sequence AGGACGTTGGGGTTAGGG-GAGGACAGTG; SEQ ID NO: 9) and the rat α-myosin heavy chain T3RE (i.e., of sequence CTGGAGGTGACAG-GAGGACAGCAGCCCTGA; SEQ ID NO: 7), which do not respond to RARs, did not respond to CAR.

The activation of the RARβ element by CAR is not affected by several treatments that activate or inactivate signal transduction pathways mediated by protein kinases A or C. Thus, CAR activation was not altered by addition of dibutyryl cyclic AMP, by short or long term treatments with phorbol esters, or by cotransfections with vectors expressing the specific protein kinase A inhibitor peptide.

The activation of the RAREs by CAR suggests that this orphan could play an important role in the complex regulatory network that controls expression of RA responsive genes. To examine the functional interactions between CAR and RARβ, expression vectors for both were mixed in cotransfections. Increasing amounts of the CAR expression vector were added to a βRARE (SEQ ID NO: 5)-containing CAT reporter plasmid and a fixed amount of RARβ expression vector corresponding to approximately ⅔ of the level that is saturating for induction. In the absence of RA, the increasing amount of CAR led to an increase in basal expression. In the presence of RA, the high level of activated expression was not strongly affected by addition of CAR. Together, these effects resulted in a significant decrease in the RA induction ratio with increasing amounts of CAR.

These results indicate that the two superfamily members function independently at this response element. Analogous results were obtained when increasing amounts of RARβ were added to a subsaturating amount of CAR expression vector. In the absence of RA, the constitutive activation conferred by CAR could be blocked by excess RARβ. This is consistent with previous reports that RARs can repress expression in the absence of ligand. When retinoic acid was added, activation was observed at even moderate levels of RARβ. The levels of activated expression associated with the various doses of RARβ vector were similar to those observed in the absence of cotransfected CAR. It therefore seems most likely that CAR and RARβ do not interfere with each other when co-expressed at moderate levels. Under other circumstances, more complex indirect effects could be anticipated for the interaction between CAR and RXR (see below).

In contrast, addition of low levels of RXRα stimulated the effect of a subsaturating dose of CAR expression vector. Since similar results are observed with the receptors able to heterodimerize with RXRs, this result strongly suggests that RXRα may share a similar interaction with CAR.

DNA Binding by Human CAR

To confirm that CAR binds the βRARE, nuclear extracts from HeLa cells infected with vaccinia virus vectors overexpressing FLAG epitope-tagged versions of CAR or RARα were used in standard gel shift experiments. Both CAR- and RARα-containing extracts showed specific binding to the RARβ element (SEQ ID NO: 5), with RAR binding being of higher apparent affinity. In agreement with results of cotransfections, CAR binding was strongly stimulated by addition of nuclear extract from vaccinia infected HeLa cells overexpressing RXRα. However, little or no effect on affinity was observed when CAR and RAR were mixed. No evidence for formation of CAR/RAR heterodimers was observed in gels electrophoresed for longer times to better resolve the CAR and RAR shifted complexes. From these results, it appears that CAR can bind directly to the RARβ element, and that binding is strongly stimulated by RXRα.

The constitutive activity of CAR may be due to either a truly constitutive transcriptional activation function or the presence of some ubiquitous ligand. The former possibility is supported by its activity in serum free media and in distinct cell types. The existence of a ligand may be favored by the somewhat lower relative activity observed with serum free medium compared to medium containing charcoal stripped serum. However, the substantial changes in the expression of the control and activated promoters under these two quite distinct growth conditions suggest that less specific or direct effects could explain this difference.

Negative results have been obtained by several approaches designed to determine whether the constitutive activation of CAR is associated with various second messenger pathways. Evidence obtained to date indicates that CAR function is not affected by activation or repression of the activity of protein kinases A or C.

Based on the results presented here, it is possible that CAR plays two important roles in the complex, interlocking set of proteins that determines responses to RA, T3 and vitamin D. The first is to maintain a basal level of expression of a subset of RA responsive genes in the absence of the ligand. In the case of a cell expressing only RARβ, for example, this could allow expression of sufficient levels of the receptor to allow autoactivation of the RA-dependent positive feedback loop that regulates RARβ expression upon addition of ligand. The second potential function, is based on the interaction of CAR with RXR. Increasing expression of CAR would be expected to decrease the amount of RXR available for interaction with other heterodimeric partners. Thus, in a cell with limiting amounts of RXR, alterations in the amount or activity of CAR protein could have significant effects on the activity of RARs, T3Rs or VDR. Although the levels of CAR used in the cotransfections reported here did not show an antagonistic effect on RAR activity, preliminary results indicate that inhibitory effects of this type can be observed in other circumstances. Given the remarkable complexity of the regulatory networks that control response to the retinoids and the other ligands of this subgroup of the nuclear receptor superfamily, it is likely that even more complicated functions will be found for CAR.

Isolation of Murine CAR Receptors

A number of mouse CAR cDNA clones were isolated by standard techniques from a liver cDNA library using an hCAR (MB67) probe. Of 9 independent clones examined in detail, 4 had an intact ligand binding domain, as judged by comparisons to hCAR and other superfamily members. 3 had an internal deletion of 107 amino acids. Representative sequences of these clones have been submitted to GenBank. One additional clone included 188 bp of intron derived sequences; it is unclear whether this clone corresponded to an authentic variant or a contaminating nuclear precursor. The mCAR2 sequence used for further experiments corresponded to the cDNA clone with the most extensive 5' untranslated sequences, and the internal deletion. To generate the mCAR1 sequence used, the deleted region in this mCAR2 clone was replaced with the corresponding fragment from a clone that did not carry the deletion.

Characterization of these clones indicated that mCAR1 and hCAR shared a high degree of sequence identity throughout the DNA and ligand binding/dimerization domains (FIGS. 3A and 3B). Both proteins had very short N-terminal regions. mCAR2 was identical to mCAR1 except for an out-of-frame 107 bp deletion in the ligand binding/dimerization domain. As a consequence of this deletion, only 6 new amino acids in mCAR2 substituted for the last 78 residues of mCAR1. This C-terminal region of mCAR1 included both the heterodimerization interface referred to as the 9th heptad (Forman et al., *Mol. Endocrinol.* 4:1293–1302, 1990, Forman et al., *Mol. Endocrinol.* 3:1610–1626, 1987) or the I box (Perlmann et al., *Mol. Endocrinol.* 10:958–966, 1996), and the AF-2 transactivation domain (Danielian et al., *EMBO J.* 11:1025–1033, 1992). hCAR and mCAR belong to a small, rather divergent subgroup within the nuclear hormone receptor superfamily that also includes an orphan receptor from *Xenopus laevis* (Smith et al., *Nucl. Acids Res.* 22:66–71, 1994) and the mammalian vitamin D receptor. hCAR and mCAR also showed relatively strong similarity with the insect ecdysone receptor in the DNA binding domain, but not other domains (FIG. 3B).

Two lines of evidence demonstrated that mCAR2 was not a cloning artifact. The first was simply that this 107 bp segment was missing in more than 5 independently isolated cDNAs. The second was a more direct demonstration of the existence of bands of the expected size using PCR with primers from the E domain and polyA$^+$ mRNA from mouse liver as template. As shown in FIGS. 4A and 4B, the identity of these bands was confirmed by Southern blotting with probes containing either ligand/dimerization domain sequences present in both, or only sequences from exon 8. This analysis indicated that the mCAR2 variant was a relatively minor fraction of the total mRNA. In addition to these two species, an even lesser amount of an additional species larger than the mCAR1 product was also observed. Its size indicated that it corresponded to a nuclear precursor that included intron 7, which interrupted the coding region at the start of the mCAR2 deletion. A cDNA clone including only this intron was isolated, but it was unclear whether it represented an additional variant mRNA or a partially spliced nuclear precursor.

The similarity between the human hCAR and murine mCAR sequences was significantly less than the 90% or greater identity usually shared by true receptor homologs in different mammalian species. It was comparable to that shared by the various isoforms of the RARs, for example, suggesting that hCAR and mCAR were derived from distinct genes that encode two CAR isoforms.

Structure of the Murine CAR Gene

A single clone containing the mCAR gene was obtained from a screen of a mouse genomic library. A NotI fragment containing the entire mCAR gene and 5' and 3' flanking regions was subcloned and sequenced in its entirety. This sequence has been submitted to GenBank. As diagrammed in FIG. 5A, the murine mCAR gene was interrupted by eight introns. Exon 8 was absent in mCAR2, demonstrating that this variant was generated by alternative mRNA splicing. The 5' end of the mCAR transcript was mapped by primer extension (FIG. 5B).

Expression of the Murine CAR Gene

To carry out an analysis of murine CAR expression, a Northern blot containing 2 $\mu$g of polyA$^+$ mRNA from a variety of tissues was obtained from Clontech, Inc. and hybridized sequentially with either a full length mCAR probe or smaller probes generated by PCR. The N-terminal probe, consisting of 167 bp from the 5' untranslated region, and the C-terminal probe, consisting of the last 200 bp of the mCAR1 coding region, were generated by PCR using the mCAR1 cDNA as a template. (5' untranslated region primers: 5' TTCCTACCTACATATGGC 3' (SEQ ID NO: 13) and 5' GACCCTGCTTTCCTTGAGAT 3' (SEQ ID NO: 14); C-terminal primers: 5'AGTCGATCCTCCACTTCCAT 3' (SEQ ID NO: 15) and 5' ACTGCAAATCTCCCCGAG-CAGCG 3' (SEQ ID NO: 16)). A 210 bp 3' flanking probe extending from a position 130 bp downstream of the polyA addition site was generated by PCR using the genomic mCAR clone as template. (Primers: 5' TAGGAGGTRGAC-TAGAGTTCCTTCT 3' (SEQ ID NO: 17) and 5' GAT-TGAGATATTACTACTCCTTTCTTC 3' (SEQ ID NO: 18)). Prior to each rehybridization, the membrane was exposed for at least 2 days to confirm the removal of the previous probe.

Standard conditions (Ausubel et al., *Current Protocols in Molecular Biology*, Greene Pub. Assoc.: New York, 1997) were used for mRNA based PCR with mouse liver mRNA as a template and primers from exons 7 and 9. For Southern analysis of the PCR products, probes corresponded to a restriction fragment containing the mCAR1 ligand binding domain, or a shorter segment derived solely from exon 8. Standard conditions (Ausubel et al., *Current Protocols in Molecular Biology*, Greene Pub. Assoc.: New York, 1997) were used for primer extension analysis with total mouse liver RNA, and the primer 5' TGCCTCAGTGCCTG-GAAAACAAGGGCCTTCTCTTGC 3' (SEQ ID NO: 19) derived from the mCAR 5' untranslated region.

Results from these experiments are shown in FIG. 6. In Northern blots of polyA$^+$ RNA from various mouse tissues hybridized at high stringency with CAR probes, mCAR expression was by far the highest in liver, as previously described for hCAR. In both mouse and human, the most prominent product was a rather broad band of approximately 1.3 to 1.7 kb At least in mouse, this band presumably included both mCAR1 and mCAR2 transcripts. Additional species of approximately 3.0, 4.0, and 5.7 kb were observed in mouse. Larger transcripts of somewhat different sizes were also present in human liver mRNA. All of these larger mouse transcripts were also identified by much smaller probes containing only 5' untranslated or ligand/dimerization domain sequences (FIG. 6). The hybridization of the 5' probe indicated that these various species did not correspond to variants with distinct N-terminal sequences, as observed, for example, with TRβ1 and TRβ2 (Hodin et al., *Science* 244:76–99, 1989). Similarly, the identical pattern of hybridization with the ligand/dimerization probe indicated that the various transcripts did not include major substitutions of sequences in that region. Finally, a probe from the 3' flanking region of the gene, hybridized only to the three larger species. Thus, these larger species were presumably generated as a consequence of a lack of addition of a polyA tract at the position used for the shorter transcripts. These longer, read-through transcripts must include extensive additional 3' untranslated regions, but it is not known whether the different larger species are generated by additional cases of alternative poly A addition, or by alternative mRNA splicing.

In much longer exposures of hybridizations with either the full length probe or the two probes from the 3' end, an additional transcript of approximately 2.8 kb was observed in heart, brain, skeletal muscle, and kidney. This did not correspond in size to any of the liver transcripts, and could have been either a transcript of the true murine homolog of hCAR, or another variant product of the mCAR gene.

DNA Binding by mCAR1 and mCAR2

For DNA binding studies, mCAR1, mCAR2, RAR, and RXR proteins were expressed using coupled in vitro transcription and translation (Promega, Inc.). Standard conditions were used for electrophoretic mobility shift assays with the DR-5 response element from the RARβ2 promoter (the βRARE) as the probe, as described for hCAR (MB67). In these experiments, mCAR1/RXR heterodimers bound with high affinity to the RARE from the RARβ2 isoform promoter (Sucov et al., Proc. Natl. Acad. Sci. USA 87:5392–5396, 1990; de The et al., Nature 343:177–180, 1990) (FIG. 7). As with hCAR, the apparent affinity of mCAR1/RXR heterodimers for this βRARE element was indistinguishable from that of RAR/RXR heterodimers. mCAR2 did not bind the βRARE or any other element tested either alone or with RXR. This lack of mCAR2 binding was consistent with the absence of the C-terminal portion of the ligand/dimerization domain, which is essential for heterodimerization.

Transactivation by mCAR1 and mCAR2

To determine whether mCAR1 transactivated the βRARE in the absence of retinoids or any other exogenously added ligands, this construct was cotransfected with a luciferase reporter plasmid in which 3 copies of the βRARE were inserted upstream of the TK promoter. To carry out these experiments, HepG2 cells were maintained and transfected using calcium phosphate or DEAE dextran (Ausubel et al., Current Protocols in Molecular Biology, Greene Pub. Assoc.: New York, 1997). mCAR1 and mCAR2 expression vectors were generated by inserting appropriate fragments into the vector CDM8 (Seed, Nature 329:840–842, 1987), as previously described for hCAR. The luciferase reporter plasmid (Gulick et al., Proc. Natl. Acad. Sci. USA 91:11012–11016, 1994) contained three copies of the βRARE upstream of the TK promoter. The reporter plasmids with wild type and mutant versions of the RARβ2 promoter have been described (Moghal et al., Mol. Cell. Biol. 15:3945–3959, 1995). Transfections also included the pTKGH control plasmid which directed expression of human growth hormone (Selden et al., Mol. Cell. Biol. 6:3173–3179, 1986). Luciferase activities were normalized using levels of growth hormone expression.

For the TK reporter, pairs of 30 mm dishes were each transfected with 2 μg of reporter and pTKGH, and a total of 2 μg of mammalian expression vector. For the RARβ2 reporters, pairs of 30 mm dishes were each transfected with 1.5 μg of the reporter and of the mammalian expression vector, and 2 μg of the pTKGH control. Transfections were carried out in media containing 10% charcoal stripped serum, and luciferase activity was determined using the Promega luciferase assay system as described by the manufacturer. Luciferase values were normalized using the growth hormone expression directed by the TKGH internal control.

The results of these experiments are shown in FIGS. 8A and 8B. In various cell types and under a variety of conditions, hCAR transactivated this reporter approximately 20–100 fold, while mCAR1 was somewhat more effective, conferring a 50 to 300 fold activation (FIG. 8A). In the presence of all-trans retinoic acid, RAR was an even more potent transactivator of this reporter. As with hCAR, the apparently constitutive transactivation by mCAR1 was observed in the presence of serum treated with charcoal to remove retinoids or other potential ligands, and in several different cell types. As shown in FIG. 8A, mCAR2 did not transactivate this element, and also did not affect transactivation by hCAR or mCAR1. Similar results were obtained with higher ratios of mCAR2. As expected from these results, mCAR1, but not mCAR2, was able to transactivate a reporter containing the intact RARβ2 promoter, but not a mutant version in which the βRARE element was inactivated by point mutations (FIG. 8B).

To confirm that the transactivation observed was a direct effect of mCAR1, mutations were introduced into the mCAR1 AF-2 region. These mutations included both simple deletions and point mutants that were chosen based on comparisons of this region of mCAR to the analogous region in other receptors. As indicated in FIG. 9A, the D8 mutation and the point mutants L353A and E355A specifically affected the AF-2 motif. The larger D27 mutation extended into the region homologous to helix 10 of RXR (Bourget et al., Nature 375:377–382, 1995), and the analogous helices in the TR (Wagner et al., Nature 378:690–697, 1995) and RAR (Renaud et al., Nature 378:681–689, 1995) structures, but stopped short of the 9th heptad motif (Forman et al., Mol. Endocrinol. 4:1293–1302, 1990) within this helix. All of these mutations completely abrogated transactivation by mCAR1 (FIG. 9B). A Western blot with an antibody directed against an epitope tag present at the N-terminus of the wild type and mutant proteins confirmed that all were expressed at similar levels. To confirm expression of mutant derivatives of mCAR1, whole cell extracts were prepared from appropriately transfected COSM6 cells as described (Ladias et al, J. Biol. Chem. 267:15849–15860, 1992). COSM6 cells do not express endogenous CAR proteins. These extracts were supplemented similarly prepared COSM6 expressed RXR and used for electrophoretic mobility shift analysis using standard conditions.

As demonstrated in FIG. 9C, all the mutants except D27 were able to bind DNA. Although this mutant retained the 9th heptad motif, it was missing most of the helix that contained this motif. At least in the case of RXR homodimers, the C-terminus of this helix is involved in an important dimer contact (Bourget et al., Nature 375:377–382, 1995).

mCAR Isoforms

Many of the genes that encode the members of the nuclear hormone receptor superfamily express more than one protein product as a consequence of either alternative promoter utilization or alternative mRNA processing. The independent isolation of a number of cDNA clones corresponding to the deleted mCAR2 product initially suggested that the mCAR gene belonged to this group, and the existence of distinct mCAR isoforms was confirmed by a PCR based approach. The mCAR gene also expressed additional transcripts with larger 3' untranslated sequences as a consequence of a lack of poly A addition at the primary site. However, these larger transcripts did not encode variant mCAR proteins.

The mCAR1 and hCAR sequences contained a good match to the AF-2 transcriptional activation domain at their extreme C-termini. This conserved motif is present in many conventional receptors and orphans (Danielian et al., *EMBO J.* 11: 1025–1033, 1992), and has been directly associated with ligand dependent transcriptional activation in several conventional receptors (e.g., (Barettino et al., *EMBO J.* 13:3039–3049, 1994; Tone et al., *J. Biol. Chem.* 269:31157–31161, 1994, Tate et al., *Mol. Cell. Biol.* 14:2323–2330, 1994; and vom Baur et al., *EMBO J.* 15:110–124, 1996)). Mutation of this conserved motif in mCAR also blocked transactivation. This demonstrated that the CAR component of the CAR/RXR heterodimer was actively involved in transactivation. It also confirmed a prediction, derived from both sequence conservation and recent results with HNF-4 (Malik et al., *Mol. Cell. Biol.* 16:1824–1831, 1996), that the conserved AF-2 motif is involved not only in ligand dependent transactivation, but also in the apparently ligand independent transactivation observed with several other orphans.

The mCAR2 variant was missing an additional conserved motif near the C-terminus of the ligand binding/dimerization domain, which has been called the 9th heptad (Forman et al., *Mol. Endocrinol.* 4:1293–1302, 1990; Forman et al., *Mol. Endocrinol.* 3:1610–1626, 1987) or the I-box (Perlmann et al., *Mol. Endocrinol.* 10:958–966, 1996). A number of studies with diverse receptors have shown that this region is required for heterodimerization with RXR (e.g., Au-Fliegner et al., *Mol. Cell. Biol.* 13:5725–5737, 1993). Since heterodimerization is required for high affinity DNA binding, it is not surprising that the mCAR2 variant did not bind the βRARE or other elements. Particularly since mCAR2 was also missing the conserved AF-2 transactivation motif, it should not compete for coactivator binding, and should not inhibit transactivation by mCAR1, a prediction borne out in appropriate transfections. This leaves the function of the mCAR2 variant undefined, though it is possible that it could compete with the mCAR1 form for interaction with other, as yet undefined, proteins.

Previous results have demonstrated a positive feedback loop in which the RARβ2 transcript is strongly induced by retinoids (Sucov et al., *Proc. Natl. Acad. Sci. USA* 87:5392–5396, 1990; de The et al., *Nature* 343:177–180, 1990). Although the levels of the RARβ2 transcript are very low in the absence of retinoids in some cultured cell lines, this transcript is present at significant levels in the livers of vitamin A deficient animals (Haq et al., *Proc. Natl. Acad. Sci. USA* 88:8272–8276, 1991). The combination of the expression of mCAR1 in the liver and its ability to transactivate the RARP2 promoter in the absence of any added retinoids clearly suggests a direct role for this orphan in maintaining basal levels of RARβ2. From a broader perspective, it seems likely that mCAR1 also acts to maintain expression of other retinoid responsive genes in the absence of retinoids.

As previously discussed for hCAR, mCAR1 could have more complex effects in the presence of retinoids. Since it is a less potent transactivator than RAR, it could act to decrease overall expression by competing for occupancy if both proteins were present at high levels. If both CAR and RAR were present at subsaturating levels, however, additional occupancy of RAREs by CAR might augment RAR action. The apparent ability of endogenous RARs to fully occupy specific RAREs under at least some in vivo conditions (Dey et al., *Mol. Cell Biol.* 14:8191, 1994) suggests that competition for binding could be an important aspect of CAR function. In contrast, the observation that supraphysiologic expression of a receptor usually substantially augments response (e.g., Brent et al., *J. Biol. Chem.* 264:178, 1989; Webb et al., *Mol. Endocrinol.* 6:157, 1992) is consistent with the possibility that CAR cooperates with the RARs.

The relative roles of CAR and RAR on a particular element are clearly dependent, not only on their relative levels of expression, but also on their relative DNA binding affinities. mCAR1/RXR heterodimers, like hCAR/RXR heterodimers, bound the βRARE with an affinity indistinguishable from that of RAR/RXR heterodimers, and CAR/RXR complexes can also bind with high affinity to other DR-5 and DR-2 RAREs. Unexpectedly, however, recent results have demonstrated that the affinity of CAR/RXR heterodimers, but not RAR/RXR heterodimers, for DR-5 sites is strikingly dependent on the sequence of the 5 base pair spacer. This suggests that CAR targets only a subset of retinoid responsive genes, and provides yet another example of the complexity of the overlapping network of regulatory effects of the nuclear hormone receptors.

Polypeptide Expression

Polypeptides according to the invention may be produced by transformation of a suitable host cell with all or part of a CAR receptor-encoding cDNA fragment (e.g., the cDNA described above) in a suitable expression vehicle.

Those skilled in the field of molecular biology will understand that any of a wide variety of expression systems may be used to provide the recombinant receptor protein. The precise host cell used is not critical to the invention. The CAR receptor may be produced in a prokaryotic host (e.g., *E. coli*) or in a eukaryotic host (e.g., *Saccharomyces cerevisiae* or mammalian cells, e.g., COS 1, NIH 3T3, and JEG3 cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1989). The method of transfection and the choice of expression vehicle will depend on the host system selected. Transformation and transfection methods are described, e.g., in Ausubel et al. (*Current Protocols in Molecular Biology*, John Wiley & Sons, New York, 1989); expression vehicles may be chosen from those provided, e.g., in *Cloning Vectors*: A Laboratory Manual (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a CAR receptor polypeptide would be inserted into the pMAMneo vector in an orientation designed to allow expression. The recombinant receptor protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, a CAR receptor polypeptide is produced by a stably-transfected mammalian cell line.

A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the receptor polypeptide is cloned into an expression vector which includes the dihydrofolate reductase (DHFR) gene. Integration of the plasmid and, therefore, the CAR receptor-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

Once the recombinant CAR receptor polypeptide is expressed, it is isolated, e.g., using affinity chromatography. In one example, a CAR binding site (e.g., the βRARE site described above) or an anti-CAR receptor antibody (e.g., produced as described below) may be attached to a column and used to isolate the receptor polypeptide. Lysis and fractionation of receptor-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Receptors of the invention, particularly short receptor fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful CAR receptor fragments or analogs (described below).

Identification of Ligands which Bind CAR Receptors

Although the human CAR receptor described above was capable of activating some level of target gene expression in the apparent absence of a ligand, this does not discount the possibility that the receptor interacts with one or more ligands, e.g., to modulate receptor activity. Moreover, it is possible that multiple CAR receptors exist (e.g., as the products of a differentially-spliced CAR mRNA) and that different receptor species interact with different ligands. Accordingly, one aspect of the invention features a screening assay for the identification of compounds which specifically bind to the CAR receptors described herein. Such an assay may be carried out using a recombinant receptor protein.

In one example, the CAR receptor component is produced by a cell that naturally produces substantially no receptor or by a cell which produces functionally deficient receptor (i.e., a cell which apparently expresses CAR receptor mRNA as measured by Northern blotting but which does exhibit reporter gene induction, in the absence of recombinantly-produced CAR receptor, in a transactivation assay, see below); suitable cells are, e.g., those discussed above with respect to the production of recombinant receptor, most preferably, mammalian cells such as JEG3 cells. Host cells are transfected with (1) a vector which expresses a nucleic acid encoding the CAR receptor component (i.e., the "producer vector") and (2) a vector which includes a CAR receptor binding site (e.g., the βRARE sequence GGG-TAGGGTTCACCGAAAGTTCACTCG; SEQ ID NO: 5; described above) positioned upstream of a target gene which may be assayed (e.g., a CAT gene or a β-galactosidase gene) (i.e., the "reporter vector"). Using such a standard transactivation assay procedure, CAR receptor activity is assayed by measuring CAR binding site-dependent target gene expression. CAR ligands are identified as those compounds which, when added to the host cell medium, effect a change in CAR receptor-directed gene expression (as detected using any CAR reporter vector); a CAR ligand according to the invention may either increase CAR receptor activity or decrease CAR receptor activity.

Any suitable transactivation technique, CAR receptor-encoding producer vector, and CAR receptor binding site-containing reporter vector may be used. Descriptions of transactivation assays and generally useful vectors for the identification of ligands which bind other nuclear hormone receptors are described, e.g., in Evans et al. (U.S. Pat. No. 4,981,784, 1991); Evans et al. (WO 90/07517); Evans et al. (WO90/01428); and WO88/03168; all hereby incorporated by reference. CAR receptor polypeptides which may be used to screen for CAR ligands include wild-type molecules as well as any appropriate chimeric receptor, for example, the GR/CAR and TR/CAR receptors described above.

Candidate ligands may be purified (or substantially purified) molecules or the ligand may be one component of a mixture of ligands (e.g., an extract or supernatant obtained from cells; Ausubel et al., supra). In a mixed ligand assay, the CAR ligand is identified by testing progressively smaller subsets of the ligand pool (e.g., produced by standard purification techniques, e.g., HPLC or FPLC) until a single ligand is finally demonstrated to modulate the CAR receptor gene stimulatory activity. Candidate CAR ligands include peptide as well as non-peptide molecules.

Alternatively, a ligand may be identified by its ability to bind a CAR receptor polypeptide using affinity chromatography. Recombinant receptor is purified by standard techniques, from cells engineered to express the receptor (e.g., those described above); the recombinant receptor immobilized on a column (e.g., a Sepharose column or a streptavidin-agarose column by the immunoaffinity method of Ausubel et al., supra) and a solution containing one or more candidate ligands is passed through the column. Such a solution (i.e., such a source of candidate ligands) may be, e.g., a cell extract, mammalian serum, or growth medium on which mammalian cells have been cultured and into which the cells have secreted factors (e.g., growth factors) during culture; again, candidate CAR ligands include peptide as well as non-peptide molecules. A ligand specific for a recombinant receptor is immobilized on the column (because of its interaction with the receptor). To isolate the ligand, the column is first washed to remove nonspecifically bound molecules, and the ligand of interest is then released from the column and collected.

CAR ligands isolated by the above methods (or any other appropriate method) may, if desired, be further purified (e.g., by high performance liquid chromatography; see above). Once isolated in sufficiently-purified form, a novel peptide ligand may be partially sequenced (by standard amino acid sequencing techniques). From this partial amino acid sequence, a partial nucleic acid sequence is deduced which allows the preparation of primers for PCR cloning of the ligand gene (e.g., by the method of Ausubel et al., supra).

Identification of CAR Receptor DNA Binding Sites

Identification of the CAR receptor facilitates identification of its DNA binding site(s). According to one approach, CAR receptor DNA binding sites may be identified using a transactivation assay, e.g., as described above for the identification of the binding site of sequence GGGTAGGGT- TCACCGAAAGTTCACTCG (SEQ ID NO: 5). Briefly, candidate DNA binding sites are inserted upstream of a target gene (whose expression may be assayed, e.g., those genes described above) and the ability of a CAR receptor polypeptide to bind the DNA site is assayed as its ability to activate downstream gene expression.

Alternatively, a DNA binding site may be identified by selectively retaining a receptor-bound DNA fragment on a nitrocellulose filter. This approach relies on the ability of nitrocellulose to bind proteins but not double-stranded DNA. Purified CAR receptor polypeptide (e.g., purified by standard techniques from cells engineered to express the receptor, e.g., those described above) is mixed with labelled double-stranded DNA (e.g., a random pool of DNA fragments) under conditions which allow interaction. After incubation, the mixture is suction filtered through nitrocellulose, allowing unbound DNA to pass through the filter while retaining the protein and any DNA specifically bound to it. Bound DNA fragments are then eluted from the filter and analyzed by gel electrophoresis or amplification and cloning. A detailed description of this technique is published in Ausubel et al., supra).

Candidate DNA fragments for either approach may be derived from a randomly cleaved or sonicated genomic DNA library and/or may be derived from known nuclear hormone response elements (see, e.g., Evans et al., WO90/11273).

Identification of CAR receptor DNA binding sites facilitates a search for the presence of such sites upstream of known or yet unidentified genes (e.g., by an examination of sequences upstream of known genes or by standard hybridization screening of a genomic library with binding site probes). CAR-mediated transcriptional control of genes bearing the binding site upstream may then be investigated (e.g., by transactivation experiments as described above), potentially leading to the elucidation of novel CAR receptor functions.

Chimeric Receptors

The functional domains of the CAR receptor may be swapped with the domains of other members of the nuclear hormone receptor family (see, e.g., Evans et al., WO 90/11273; Evans, *Science* 240:889, 1988) in order to produce receptors having novel properties. For example, if the DNA binding domain of the glucocorticoid receptor were fused to the gene activation domain of the CAR receptor, a novel receptor would be produced which could bind genes bearing an upstream glucocorticoid response element and activate gene expression in the absence of hormone. Conversely, fusion of the CAR DNA binding domain to the ligand-binding and gene activation domains of glucocorticoid receptor would confer hormonal regulation on genes downstream of CAR binding sites. Finally, fusion of the CAR DNA binding domain to a trans-repressing domain (see, e.g., Evans et al., WO90/14356) would result in repression of the basal level of expression of genes bearing upstream CAR binding sites. Construction of receptor fusion genes is carried out by standard techniques of molecular biology. CAR receptor domains are as follows: DNA binding domain, approximately amino acids 11–76; and gene activation and potential ligand binding domain, approximately amino acids 76–348. Examples of receptor domains which may be included in a chimeric CAR receptor are described in Evans et al. (WO 90/15815) and in Evans et al. (*Science* 240:889, 1988).

Dominant Negative Mutants

Mutants of the CAR receptor may be generated which interfere with normal CAR receptor activity. Such mutants are termed "dominant negative" and fall into at least two classes: (a) ones which bind to their DNA binding site (thereby interfering with the ability of wild-type receptor to bind the same site) and which do not activate gene expression and (b) ones which heterodimerize with other receptors (e.g., RXR) but which do not promote the biological response associated with the wild-type heterodimer.

The first class of CAR dominant negative mutants include those receptor polypeptides which contain a wild-type DNA binding domain and a mutant gene activation domain. Such mutants are unable to transactivate a reporter gene (e.g., as measured using a CAT reporter gene with an upstream βRARE and the standard methods described above) but retain the ability to bind a CAR DNA binding site (as evidenced, e.g., by DNA footprint analysis using a βRARE DNA sequence; Ausubel et al., supra).

The second class of CAR dominant negative mutants include those receptor polypeptides which contain a wild-type heterodimerization domain. Such a mutant interacts with its heterodimer partner and disrupts the partner's function. In one particular example, a dominant negative CAR receptor polypeptide may be overproduced (e.g., by directing its expression from a very strong promoter); the abundant CAR receptor polypeptide forms heterodimers with cellular RXR protein, soaking up available RXR and thereby preventing RXR homodimer formation as well as RXR heterodimer formation with other partner proteins (e.g., RAR, VDR, and T3R). Wild-type CAR receptor polypeptide may function as a dominant negative mutant if overproduced in this manner. However, a mutant CAR receptor lacking a gene activation domain (e.g., as identified above) and/or a DNA binding domain (e.g., as identified by DNA footprint analysis, above) is preferred.

Any of the above mutants may be generated by any method of random or site-directed DNA mutagenesis (see, e.g., Ausubel et al., supra).

Identification of Molecules which Modulate CAR Receptor Expression

Isolation of CAR receptor genes also facilitates the identification of molecules which increase or decrease CAR receptor expression, and which may be useful as therapeutics, e.g., for treatment of cancers such as lung cancer, or for treatment of thyroid disorders such as Graves' disease. According to one approach, candidate molecules (e.g., peptide or non-peptide molecules found, e.g., in a cell extract, mammalian serum, or growth medium on which mammalian cells have been cultured) are added at varying concentrations to the culture medium of cells which express CAR receptor mRNA (e.g., HepG2, JEG-3, or HeLa cells). CAR receptor expression is then measured by standard Northern blot analysis (Ausubel et al., supra) using CAR receptor cDNA as a hybridization probe. The level of CAR receptor expression in the presence of the candidate molecule is compared to the level measured for the same cells in the same culture medium but in the absence of the candidate molecule. A molecule which promotes an increase or decrease in CAR receptor expression is considered useful in the invention.

Anti-CAR Receptor Antibodies

Human or murine CAR receptor (or immunogenic receptor fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the CAR polypeptides described above and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific CAR receptor recognition by Western blot or immunoprecipitation analysis (by the methods described in Ausubel et al., supra). Antibodies which specifically recognize a CAR receptor polypeptide are considered to be useful in the invention; such antibodies may be used, e.g., in an immunoassay to monitor the level of CAR receptor produced by a mammal.

Therapy

Because a lack of retinoic acid receptor has been associated with the occurrence of lung cancer and because the CAR receptor polypeptide binds and activates expression of the retinoic acid receptor gene, it is likely that the administration of a CAR receptor polypeptide to a mammal may prevent or treat cancers, particularly lung cancer. Similar therapeutic results would be expected for administration of a ligand which stimulates CAR receptor activity.

CAR receptor polypeptides may also find therapeutic use in the treatment of Graves disease, a disease resulting from an increase in thyroid hormone receptor function. RXR protein plays a role in thyroid hormone receptor expression. Accordingly, dominant negative CAR mutants which heterodimerize with RXR protein (including overexpressed wild-type CAR receptor protein) may act to decrease the cellular levels of available RXR and thereby decrease thyroid hormone receptor function. Again, ligands which increase heterodimerization efficiency could also be administered as a treatment for Graves' disease.

To treat the above diseases, the appropriate CAR receptor polypeptide (or ligand) is administered as a therapeutic preparation (e.g., in physiological saline) in accordance with the condition to be treated. Ordinarily, it will be administered intravenously, at a dosage effective to increase retinoic acid receptor expression (as a cancer treatment) or effective to decrease thyroid hormone receptor function (as a treatment for Graves' disease). Alternatively, it may be convenient to administer the therapeutic orally, nasally, or topically, e.g., as a liquid or a spray. Again, the dosages are as described above. Treatment may be repeated as necessary for alleviation of disease symptoms.

The methods of the invention may be used to reduce the disorders described herein in any mammal, for example, humans, domestic pets, or livestock. Where a non-human mammal is treated, the CAR receptor polypeptide or the antibody employed is preferably specific for that species.

Other Embodiments

Polypeptides according to the invention include the entire human or murine CAR receptor sequences (as described in FIGS. 1 and 2; SEQ ID NOS:1, 10, 11, and 12) as well as any analog or fragment of the human or murine CAR receptors which include either a DNA binding domain or gene activation domain; or which include a heterodimerization domain (as identified using the techniques described above).

Polypeptides of the invention also include all mRNA processing variants (e.g., all products of alternative splicing or differential promoter utilization) as well as CAR receptor proteins from other mammals.

Specific receptor fragments or analogues of interest include full-length or partial (see below) receptor proteins including an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the receptors' ability to either bind DNA and activate transcription; or to interact with CAR receptor's heterodimerization partners (as assayed above). Analogs also include receptor polypeptides which are modified for the purpose of increasing peptide stability; such analogs may contain, e.g., one or more desaturated peptide bonds or D-amino acids in the peptide sequence or the peptide may be formulated as a cyclized peptide molecule.

Other embodiments are within the following claims.

What is claimed is:

1. A method of identifying a CAR ligand, comprising
   (a) providing a nucleic acid sequence which encodes a CAR receptor polypeptide;
   (b) introducing into a host cell which is functionally deficient for CAR receptor (i) said nucleic acid which encodes said CAR receptor polypeptide and (ii) a reporter gene operably linked to a CAR receptor polypeptide binding site;
   (c) measuring induction of said reporter gene in said transfected host cell;
   (d) contacting said transfected host cell with a candidate ligand; and
   (e) measuring induction of said reporter gene in the presence of said candidate ligand, an increase or decrease in said induction as compared to the induction in (c) being indicative of the presence of a CAR ligand.

2. The method of claim 1, wherein said CAR receptor polypeptide comprises an amino acid sequence substantially identical to the amino acid sequence shown in FIG. 1 (SEQ ID NO: 10) or FIG. 2 (SEQ ID NO:12).

3. The method of claim 1, wherein said CAR receptor polypeptide binding site is GGGTAGGGTTCAC-CGAAAGTTCACTCG (SEQ ID NO: 5).

4. The method of claim 1, wherein said CAR receptor polypeptide is mammalian.

5. The method of claim 4, wherein said CAR receptor polypeptide is human.

6. The method of claim 1, wherein said CAR receptor polypeptide comprises the amino acid sequence shown in FIG. 1 (SEQ ID NO: 10).

7. The method of claim 1, wherein said CAR receptor polypeptide comprises:
   (i) the DNA binding domain (amino acids 11–75) of the CAR receptor sequence shown in SEQ ID NO: 10, or a sequence which differs therefrom by a single conservative amino acid substitution; and
   (ii) the gene activation domain (amino acids 76–348) of the CAR receptor sequence shown in SEQ ID NO: 10, or a sequence which differs therefrom by a single conservative amino acid substitution.

8. The method of claim 1, wherein said CAR receptor polypeptide comprises amino acids 173–319 of FIG. 1 (SEQ ID NO: 10).

* * * * *

UNITED STATES PATENT AND TRADEMARK OFFICE
CERTIFICATE OF CORRECTION

| | | |
|---|---|---|
| PATENT NO. | : 6,989,242 B1 | Page 1 of 1 |
| APPLICATION NO. | : 08/934388 | |
| DATED | : January 24, 2006 | |
| INVENTOR(S) | : Moore et al. | |

It is certified that error appears in the above-identified patent and that said Letters Patent is hereby corrected as shown below:

TITLE PAGE, ITEM (56) add the following:
Under FOREIGN PATENT DOCUMENTS
--WO  98/33819                08/1998--

TITLE PAGE, ITEM (56) add the following:
Under OTHER PUBLICATIONS
--Baes et al., "A New Orphan Member of the Nuclear Hormone Receptor Superfamily that Interacts with a Subset of Retinoic Acid Response Elements," *Molecular and Cellular Biology* 14:1544-1552 (1994).

Choi et al., EMBL MMAF 9327, Accession No. AF009327 (1997).

Tomko et al., "HCAR and MCAR:  The Human and Mouse Cellular Receptors For Subgroup C Adenoviruses and Group B Coxsackieviruses," *Proc. Natl. Acad. Sci. USA* 94:3352-3356 (1997).--

Column 16, Line 48, replace "promotor" with --promoter--.

Signed and Sealed this

Sixth Day of November, 2007

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 1450
<212> TYPE: DNA
<213> ORGANISM: Homo sapiens

<400> SEQUENCE: 1
gtgagcttgc tccttaagtt acaggaactc tccttataat agacacttca ttttcctagt      60
ccatccctca tgaaaaatga ctgaccactg ctgggcagca ggagggatga taatcctaac     120
tccaatcact ggcaactcct gagatcagag gaaaaccagc aacagcgtgg gagtttgggg     180
agaggcattc cataccagat tctgtggcct gcaggtgaca tgctgcctaa gagaagcagg     240
agtctgtgac agccacccca acacgtgacg tcatggccag tagggaagat gagctgagga     300
actgtgtggt atgtggggac caagccacag gctaccactt taatgcgctg acttgtgagg     360
```

| | |
|---|---|
| gctgcaaggg tttcttcagg agaacagtca gcaaaagcat tggtcccacc tgcccctttg | 420 |
| ctggaagctg tgaagtcagc aagactcaga ggcgccactg cccagcctgc aggttgcaga | 480 |
| agtgcttaga tgctggcatg aggaaagaca tgatactgtc ggcagaagcc ctggcattgc | 540 |
| ggcgagcaaa gcaggcccag cggcgggcac agcaaacacc tgtgcaactg agtaaggagc | 600 |
| aagaagagct gatccggaca ctcctggggg cccacacccg ccacatgggc accatgtttg | 660 |
| aacagtttgt gcagtttagg cctccagctc atctgttcat ccatcaccag cccttgccca | 720 |
| ccctggcccc tgtgctgcct ctggtcacac acttcgcaga catcaacact ttcatggtac | 780 |
| tgcaagtcat caagttttact aaggacctgc ccgtcttccg ttccctgccc attgaagacc | 840 |
| agatctccct tctcaaggga gcagctgtgg aaatctgtca catcgtactc aataccactt | 900 |
| tctgtctcca aacacaaaac ttcctctgcg ggcctcttcg ctacacaatt gaagatggag | 960 |
| cccgtgtggg gttccaggta gagttttgg agttgctctt tcacttccat ggaacactac | 1020 |
| gaaaactgca gctccaagag cctgagtatg tgctcttggc tgccatggcc ctgttctctc | 1080 |
| ctgaccgacc tggagttacc cagagagatg agattgatca gctgcaagag gagatggcac | 1140 |
| tgactctgca aagctacatc aagggccagc agcgaaggcc ccgggatcgg tttctgtatg | 1200 |
| cgaagttgct aggcctgctg gctgagctcc ggagcattaa tgaggcctac gggtaccaaa | 1260 |
| tccagcacat ccagggcctg tctgccatga tgccgctgct ccaggagatc tgcagctgag | 1320 |
| gccatgctca cttccttccc cagctcacct ggaacaccct ggatacactg gagtgggaaa | 1380 |
| atgctgggac caaagattgg gccgggttca aagggagccc agtggttgca atgaaagact | 1440 |
| aaagcaaaac | 1450 |

```
<210> SEQ ID NO 2
<211> LENGTH: 26
<212> TYPE: DNA
<213> ORGANISM: Homo sapiens
<220> FEATURE:
<221> NAME/KEY: variation
<222> LOCATION: (9)...(9)
<223> OTHER INFORMATION: n is a, t, c, or g.
<220> FEATURE:
<221> NAME/KEY: variation
<222> LOCATION: (18)...(18)
<223> OTHER INFORMATION: n is a, t, c, or g.

<400> SEQUENCE: 2
```

| | |
|---|---|
| tgygagggnt gyaaggsntt yttymg | 26 |

```
<210> SEQ ID NO 3
<211> LENGTH: 28
<212> TYPE: DNA
<213> ORGANISM: Rattus sp

<400> SEQUENCE: 3
```

| | |
|---|---|
| aaaggtaaga tcagggacgt gaccgcag | 28 |

```
<210> SEQ ID NO 4
<211> LENGTH: 31
<212> TYPE: DNA
<213> ORGANISM: Homo sapiens

<400> SEQUENCE: 4
```

| | |
|---|---|
| tgggtgaatg aggacattac tgaccgctcc g | 31 |

```
<210> SEQ ID NO 5
<211> LENGTH: 27
```

```
<212> TYPE: DNA
<213> ORGANISM: Rattus sp

<400> SEQUENCE: 5
gggtagggtt caccgaaagt tcactcg                                              27

<210> SEQ ID NO 6
<211> LENGTH: 28
<212> TYPE: DNA
<213> ORGANISM: Rattus sp

<400> SEQUENCE: 6
aaaggtaaga tcagggacgt gacctcag                                             28

<210> SEQ ID NO 7
<211> LENGTH: 30
<212> TYPE: DNA
<213> ORGANISM: Rattus sp

<400> SEQUENCE: 7
ctggaggtga caggaggaca gcagccctga                                           30

<210> SEQ ID NO 8
<211> LENGTH: 44
<212> TYPE: DNA
<213> ORGANISM: Rattus sp

<400> SEQUENCE: 8
agacaggttg acccttttc taagggctta acctagctca cctg                            44

<210> SEQ ID NO 9
<211> LENGTH: 28
<212> TYPE: DNA
<213> ORGANISM: Homo sapiens

<400> SEQUENCE: 9
aggacgttgg ggttagggga ggacagtg                                             28

<210> SEQ ID NO 10
<211> LENGTH: 348
<212> TYPE: PRT
<213> ORGANISM: Homo sapiens

<400> SEQUENCE: 10
```

Met Ala Ser Arg Glu Asp Glu Leu Arg Asn Cys Val Val Cys Gly Asp
 1               5                  10                  15

Gln Ala Thr Gly Tyr His Phe Asn Ala Leu Thr Cys Glu Gly Cys Lys
            20                  25                  30

Gly Phe Phe Arg Arg Thr Val Ser Lys Ser Ile Gly Pro Thr Cys Pro
        35                  40                  45

Phe Ala Gly Ser Cys Glu Val Ser Lys Thr Gln Arg Arg His Cys Pro
    50                  55                  60

Ala Cys Arg Leu Gln Lys Cys Leu Asp Ala Gly Met Arg Lys Asp Met
65                  70                  75                  80

Ile Leu Ser Ala Glu Ala Leu Ala Leu Arg Arg Ala Lys Gln Ala Gln
                85                  90                  95

Arg Arg Ala Gln Gln Thr Pro Val Gln Leu Ser Lys Glu Gln Glu Glu
            100                 105                 110

Leu Ile Arg Thr Leu Leu Gly Ala His Thr Arg His Met Gly Thr Met
        115                 120                 125

```
Phe Glu Gln Phe Val Gln Phe Arg Pro Pro Ala His Leu Phe Ile His
    130                 135                 140
His Gln Pro Leu Pro Thr Leu Ala Pro Val Leu Pro Leu Val Thr His
145                 150                 155                 160
Phe Ala Asp Ile Asn Thr Phe Met Val Leu Gln Val Ile Lys Phe Thr
                165                 170                 175
Lys Asp Leu Pro Val Phe Arg Ser Leu Pro Ile Glu Asp Gln Ile Ser
            180                 185                 190
Leu Leu Lys Gly Ala Ala Val Glu Ile Cys His Ile Val Leu Asn Thr
        195                 200                 205
Thr Phe Cys Leu Gln Thr Gln Asn Phe Leu Cys Gly Pro Leu Arg Tyr
    210                 215                 220
Thr Ile Glu Asp Gly Ala Arg Val Gly Phe Gln Val Glu Phe Leu Glu
225                 230                 235                 240
Leu Leu Phe His Phe His Gly Thr Leu Arg Lys Leu Gln Leu Gln Glu
                245                 250                 255
Pro Glu Tyr Val Leu Leu Ala Ala Met Ala Leu Phe Ser Pro Asp Arg
            260                 265                 270
Pro Gly Val Thr Gln Arg Asp Glu Ile Asp Gln Leu Gln Glu Glu Met
        275                 280                 285
Ala Leu Thr Leu Gln Ser Tyr Ile Lys Gly Gln Gln Arg Arg Pro Arg
    290                 295                 300
Asp Arg Phe Leu Tyr Ala Lys Leu Leu Gly Leu Leu Ala Glu Leu Arg
305                 310                 315                 320
Ser Ile Asn Glu Ala Tyr Gly Tyr Gln Ile Gln His Ile Gln Gly Leu
                325                 330                 335
Ser Ala Met Met Pro Leu Leu Gln Glu Ile Cys Ser
            340                 345

<210> SEQ ID NO 11
<211> LENGTH: 1361
<212> TYPE: DNA
<213> ORGANISM: Mus sp

<400> SEQUENCE: 11
cttgttttcc aggcactgag gaccgcagtc cctaattcct ggcagttcct gagatctcaa     60
ggaaagcagg gtcagcgagg aggcctgggg agaggaggca tcctacaccc aatcttgtgg    120
cctgctgcct aagggaaaca ggagaccatg acagctatgc taacactaga accatggcc     180
agtgaagaag aatatgggcc gaggaactgt gtggtgtgtg agaccgggc cacaggctat     240
catttccacg ccctgacttg tgagggctgc aagggcttct tcagacgaac agtcagcaaa    300
accattggtc ccatctgtcc gtttgctgga aggtgtgagg tcagcaaggc ccagagacgc    360
cactgtccag cctgcaggtt gcagaagtgt ctaaatgttg gcatgaggaa agacatgata    420
ctgtcagcag aagccctggc attgcggcga gccagacagg cacagcggcg ggcagagaaa    480
gcatctttgc aactgaatca gcagcagaaa gaactggtcc agatcctcct ggggcccac    540
actcgccatg tgggcccatt gtttgaccag tttgtgcagt tcaagcctcc agcctatctg    600
ttcatgcatc accggccttt ccagcctcgg ggccccgtgt tgcctctgct cacacacttt    660
gcagatatca cacgtttat ggtgcaacag atcatcaagt tcaccaagga tctgccgctc    720
ttccggtccc taaccatgga ggaccagatc tcccttctca agggagcggc tgtggaaata    780
ttgcatatct cactcaacac tacgttctgt cttcaaacag agaatttctt ctgtgggcct    840
cttttgctaca agatggagga cgcagtccat gcagggttcc agtacgagtt tttggagtcg    900
```

-continued

```
atcctccact tccataaaaa cctgaaagga ctgcatctcc aggagcctga gtatgtgctc      960
atggctgcca cggccctctt ctcccctgac agacccggag ttacccaaag agaagagata     1020
gatcagctac aagaggagat ggcgctgatt ctgaacaacc acattatgga acaacagtct     1080
cggctccaaa gtcggtttct gtatgcaaag ctgatgggcc tgctggctga cctccggagt     1140
ataaacaatg catactccta tgaacttcag cgcttggagg aactgtctgc tatgacgccg     1200
ctgctcgggg agatttgcag ttgaggccca ggcttgcatc ctttccccag acccccaggg     1260
atacactggc ctggaaaggg tacagcgctg accccacac gggaaccagc aggaaggagc      1320
ttgggagtgg caatgaaatg ctgaacagtc aaaaaaaaaa a                         1361
```

<210> SEQ ID NO 12
<211> LENGTH: 358
<212> TYPE: PRT
<213> ORGANISM: Mus sp

<400> SEQUENCE: 12

```
Met Thr Ala Met Leu Thr Leu Glu Thr Met Ala Ser Glu Glu Glu Tyr
1               5                   10                  15

Gly Pro Arg Asn Cys Val Cys Gly Asp Arg Ala Thr Gly Tyr His
            20                  25                  30

Phe His Ala Leu Thr Cys Glu Gly Cys Lys Gly Phe Phe Arg Arg Thr
        35                  40                  45

Val Ser Lys Thr Ile Gly Pro Ile Cys Pro Phe Ala Gly Arg Cys Glu
50                  55                  60

Val Ser Lys Ala Gln Arg Arg His Cys Pro Ala Cys Arg Leu Gln Lys
65                  70                  75                  80

Cys Leu Asn Val Gly Met Arg Lys Asp Met Ile Leu Ser Ala Glu Ala
                85                  90                  95

Leu Ala Leu Arg Arg Ala Arg Gln Ala Gln Arg Arg Ala Glu Lys Ala
            100                 105                 110

Ser Leu Gln Leu Asn Gln Gln Gln Lys Glu Leu Val Gln Ile Leu Leu
        115                 120                 125

Gly Ala His Thr Arg His Val Gly Pro Leu Phe Asp Gln Phe Val Gln
130                 135                 140

Phe Lys Pro Pro Ala Tyr Leu Phe Met His His Arg Pro Phe Gln Pro
145                 150                 155                 160

Arg Gly Pro Val Leu Pro Leu Leu Thr His Phe Ala Asp Ile Asn Thr
                165                 170                 175

Phe Met Val Gln Gln Ile Ile Lys Phe Thr Lys Asp Leu Pro Leu Phe
            180                 185                 190

Arg Ser Leu Thr Met Glu Asp Gln Ile Ser Leu Leu Lys Gly Ala Ala
        195                 200                 205

Val Glu Ile Leu His Ile Ser Leu Asn Thr Thr Phe Cys Leu Gln Thr
210                 215                 220

Glu Asn Phe Phe Cys Gly Pro Leu Cys Tyr Lys Met Glu Asp Ala Val
225                 230                 235                 240

His Ala Gly Phe Gln Tyr Glu Phe Leu Glu Ser Ile Leu His Phe His
                245                 250                 255

Lys Asn Leu Lys Gly Leu His Leu Gln Glu Pro Glu Tyr Val Leu Met
            260                 265                 270

Ala Ala Thr Ala Leu Phe Ser Pro Asp Arg Pro Gly Val Thr Gln Arg
        275                 280                 285
```

```
Glu Glu Ile Asp Gln Leu Gln Glu Glu Met Ala Leu Ile Leu Asn Asn
        290                 295                 300

His Ile Met Glu Gln Gln Ser Arg Leu Gln Ser Arg Phe Leu Tyr Ala
305                 310                 315                 320

Lys Leu Met Gly Leu Leu Ala Asp Leu Arg Ser Ile Asn Asn Ala Tyr
                325                 330                 335

Ser Tyr Glu Leu Gln Arg Leu Gly Glu Leu Ser Ala Met Thr Pro Leu
            340                 345                 350

Leu Gly Glu Ile Cys Ser
        355
```

<210> SEQ ID NO 13
<211> LENGTH: 18
<212> TYPE: DNA
<213> ORGANISM: Mus sp

<400> SEQUENCE: 13
ttcctaccta catatggc                                                    18

<210> SEQ ID NO 14
<211> LENGTH: 20
<212> TYPE: DNA
<213> ORGANISM: Mus sp

<400> SEQUENCE: 14
gaccctgctt tccttgagat                                                  20

<210> SEQ ID NO 15
<211> LENGTH: 20
<212> TYPE: DNA
<213> ORGANISM: Mus sp

<400> SEQUENCE: 15
agtcgatcct ccacttccat                                                  20

<210> SEQ ID NO 16
<211> LENGTH: 23
<212> TYPE: DNA
<213> ORGANISM: Mus sp

<400> SEQUENCE: 16
actgcaaatc tccccgagca gcg                                              23

<210> SEQ ID NO 17
<211> LENGTH: 25
<212> TYPE: DNA
<213> ORGANISM: Mus sp

<400> SEQUENCE: 17
taggaggtrg actagagttc cttct                                            25

<210> SEQ ID NO 18
<211> LENGTH: 27
<212> TYPE: DNA
<213> ORGANISM: Mus sp

<400> SEQUENCE: 18
gattgagata ttactactcc tttcttc                                          27

<210> SEQ ID NO 19
<211> LENGTH: 36
<212> TYPE: DNA

```
<213> ORGANISM: Mus sp

<400> SEQUENCE: 19
tgcctcagtg cctggaaaac aagggccttc tcttgc                                36
```